United States Patent
Bichel et al.

(10) Patent No.: US 9,968,294 B2
(45) Date of Patent: May 15, 2018

(54) MONITORING SYSTEM FOR DETERMINING THE EFFICACY OF A COMPRESSION DEVICE

(71) Applicant: 3M INNOVATIVE PROPERTIES COMPANY, Saint Paul, MN (US)

(72) Inventors: Jens Bichel, Meerbusch (DE); Joannes F. H. M. Schuren, The Netherlands (NL); Guido Hitschmann, Neuss (DE); Martin C. Neuenhahn, Duesseldorf (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 298 days.

(21) Appl. No.: 14/437,549

(22) PCT Filed: Oct. 25, 2013

(86) PCT No.: PCT/US2013/066731
§ 371 (c)(1),
(2) Date: Apr. 22, 2015

(87) PCT Pub. No.: WO2014/066714
PCT Pub. Date: May 1, 2014

(65) Prior Publication Data
US 2015/0297132 A1    Oct. 22, 2015

(30) Foreign Application Priority Data
Oct. 26, 2012    (GB) .................................. 1219242.3

(51) Int. Cl.
*A61B 5/103*    (2006.01)
*A61B 5/117*    (2016.01)
(Continued)

(52) U.S. Cl.
CPC .......... *A61B 5/4836* (2013.01); *A61B 5/0053* (2013.01); *A61B 5/0205* (2013.01);
(Continued)

(58) Field of Classification Search
CPC ..... A61B 5/4836; A61B 5/0053; A61B 5/026; A61B 5/1116; A61B 5/4848;
(Continued)

(56) References Cited

U.S. PATENT DOCUMENTS 6,231,532 B1    5/2001    Watson
7,127,370 B2    10/2006   Kelly, Jr.
(Continued)

FOREIGN PATENT DOCUMENTS

DE    19505765    10/1995
DE    20213196    1/2004
(Continued)

OTHER PUBLICATIONS

Mosti, "Comparison Between a New, Two-component Compression System with Zinc Paste Bandages for Leg Ulcer Healing: A Prospective, Multicenter, Randomized, Controlled Trial Monitoring Sub-bandage Pressures", Wounds, May 2011; vol. 23, No. 5, pp. 126-134.

(Continued)

*Primary Examiner* — Devin Henson
(74) *Attorney, Agent, or Firm* — 3M Innovative Properties Company; Lynn R. Hunsberger

(57) ABSTRACT

Disclosed is a monitoring system for determining the efficacy of at least one compression device for use in compression therapy. The monitoring system comprises at least one pressure sensor for measuring a pressure exerted onto a body part of a user by the compression device and at least one evaluation unit which is connectable to the pressure sensor. The evaluation unit is adapted to acquire at least one resting (Continued)

pressure $p_{rest}$ with the user being in a resting position. The evaluation unit is further adapted to determine at least one extended standing pressure $p_{standing,\ extended}$ with the user being in a standing position, by using the following procedure: the evaluation unit acquires a measurement curve of pressure values after a position change of the user into the standing position and a slope of the measurement curve is automatically compared to at least one endpoint threshold value and, depending on a result of the comparison, an endpoint of a change in the measurement curve induced by the position change is automatically detected, and a pressure value acquired at or after the endpoint is assigned to the extended standing pressure $p_{standing,\ extended}$.

15 Claims, 5 Drawing Sheets

(51) Int. Cl.

| | |
|---|---|
| *A61B 5/00* | (2006.01) |
| *A61B 5/11* | (2006.01) |
| *A61B 5/0205* | (2006.01) |
| *A61B 5/026* | (2006.01) |
| *A61F 13/00* | (2006.01) |
| *A61F 13/08* | (2006.01) |
| *A61B 5/02* | (2006.01) |
| *A61H 9/00* | (2006.01) |
| *A61B 5/024* | (2006.01) |

(52) U.S. Cl.
CPC ............ *A61B 5/026* (2013.01); *A61B 5/1116* (2013.01); *A61B 5/1118* (2013.01); *A61B 5/486* (2013.01); *A61B 5/4848* (2013.01); *A61B 5/4884* (2013.01); *A61F 13/00* (2013.01); *A61H 9/0092* (2013.01); *A61B 5/024* (2013.01); *A61B 5/02007* (2013.01); *A61B 5/1123* (2013.01); *A61B 5/6804* (2013.01); *A61B 5/6828* (2013.01); *A61B 2562/0247* (2013.01); *A61B 2562/0266* (2013.01); *A61F 13/08* (2013.01); *A61F 13/085* (2013.01); *A61H 9/0078* (2013.01); *A61H 2201/0184* (2013.01); *A61H 2201/5043* (2013.01); *A61H 2201/5071* (2013.01); *A61H 2201/5097* (2013.01); *A61H 2205/106* (2013.01); *A61H 2209/00* (2013.01); *A61H 2230/62* (2013.01)

(58) Field of Classification Search
CPC ............ A61B 5/6828; A61B 5/02007; A61B 2562/0247; A61F 13/08; A61F 13/085; A61H 9/0078; A61H 2201/5071; A61H 2205/106; A61H 2209/00
See application file for complete search history.

(56) References Cited

U.S. PATENT DOCUMENTS

| | | | |
|---|---|---|---|
| 2005/0107725 A1* | 5/2005 | Wild | ............... A61H 9/0071 601/152 |
| 2006/0036203 A1 | 2/2006 | Ouchene | |
| 2006/0229544 A1* | 10/2006 | Schuren | ............... A61F 13/069 602/53 |
| 2009/0055148 A1 | 2/2009 | Gobet | |
| 2009/0209830 A1* | 8/2009 | Nagle | ............... A43B 7/147 600/301 |
| 2009/0287109 A1 | 11/2009 | Ferren | |
| 2010/0010405 A1 | 1/2010 | Nardi | |
| 2011/0015498 A1 | 1/2011 | Mestrovic | |
| 2011/0196189 A1 | 8/2011 | Milbocker | |
| 2011/0319787 A1 | 12/2011 | Lamoise | |
| 2012/0065561 A1 | 3/2012 | Ballas | |
| 2012/0083712 A1 | 4/2012 | Watson | |
| 2014/0303460 A1* | 10/2014 | Corley | ............... A61B 5/6828 600/301 |

FOREIGN PATENT DOCUMENTS

| | | |
|---|---|---|
| EP | 2436349 | 4/2012 |
| GB | 2443208 | 4/2008 |
| WO | WO 2006-103422 | 10/2006 |
| WO | WO 2008-003920 | 1/2008 |
| WO | WO 2009/104127 | 8/2009 |
| WO | WO 2009/114803 | 9/2009 |
| WO | WO 2010/085111 | 7/2010 |
| WO | WO 2014-066077 | 5/2014 |

OTHER PUBLICATIONS

Partsch, "The Static Stiffness Index: A Simple Method to Assess the Elastic Property of Compression Material in Vivo", Dermatologic Surgery, Jun. 2005, vol. 31. No. 6, pp. 625-630. XP55068602.
Partsch, "The Use of Pressure Change on Standing as a Surrogate Measure of the Stiffness of a Compression Bandage", European Journal of Vascular and Endovascular Surgery, Oct. 2005, vol. 30, pp. 415-421. XP5094079.
Partsch, "Interface pressure and stiffness of ready made compression stockings: Comparison of in vivo and in vitro measurements", Journal of Vascular Surgery, Oct. 2006, vol. 44, No. 4, pp. 809-814. XP5702698.
Partsch, "Measurement of Lower Leg Compression in Vivo: Recommendations for the Performance of Measurements of Interface Pressure and Stiffness," Dermatologic Surgery, Feb. 2006; vol. 32, No. 2, pp. 224-233. XP-002718927.
International Search Report for PCT Application No. PCT/US2013/066731 dated Feb. 7, 2014, 6 pages.

* cited by examiner

MONITORING SYSTEM FOR DETERMINING THE EFFICACY OF A COMPRESSION DEVICE

CROSS REFERENCE TO RELATED APPLICATIONS

This application is a national stage filing under 35 U.S.C. 371 of PCT/US2013/066731, filed 25 Oct. 2013, which claims priority to Great Britain Application No. 1219242.3, filed 26 Oct. 2012, the disclosures of which are incorporated by reference in their entirety herein.

FIELD

The present invention refers to a monitoring system for determining the efficacy of a compression device, to a compression system and to a method for determining the efficacy of a compression device. Systems, devices and methods according to the present invention mainly are used in compression therapy, such as for treating chronic venous insufficiency. However, other fields of application are possible.

BACKGROUND

In medical technology and medicine, a plurality of treatments of a human or animal body are known which imply the use of one or more compression devices for exerting pressure onto a body or a body part such as a limb of the human or animal user. Without restricting the present invention to a specific use, the treatment of venous diseases may be named, such as chronic venous insufficiency (CVI). In CVI, generally, veins are incapable of pumping a sufficient amount of oxygen-depleted blood to the heart. This disease, mostly, is closely related to thrombosis and, in many cases, implies an insufficient function of venous valves. Venous insufficiency generally may occur in a plurality of body parts such as limbs. Most frequently, legs or parts of the leg may be affected by venous insufficiency, such as calves.

As known in the art, venous insufficiencies and/or other types of diseases may be treated by compression therapy. Therein, a pressure is exerted onto the body part affected by the respective disease. As an example, compression bandages may be used, such as single layer or multi-layer compression bandages. A plurality of bandages is commercially available, mostly flexible bandages having a specific stiffness.

When using compression therapy, a number of precautions have to be taken in order to avoid injuries by overexerting pressure to the body part on the one hand side and exerting insufficient pressure on the other hand. Therefore, a plurality of devices is known in the art for monitoring pressure exerted onto the body part during compression therapy.

In WO 2008/003920 A1, a patient compliance monitor for monitoring compliance of a patient to a treatment regime for treatment of a medical condition is disclosed. The compliance monitor comprises measurement means for measuring an external physical parameter acting on a limb of said patient, the external physical parameter having influence on the medical condition experienced by said limb. Inter alia, the use of a tilt sensor for measuring the tilt of a limb of said body, the use of a movement sensor for monitoring motion of said limb, the use of a pressure sensor for measuring the pressure applied to a region of said body, and the use of a thermometer for monitoring the ambient pressure around said body are disclosed. Further, recording means for recording data as well as comparative means for comparing the recorded data with data indicative of the treatment regime are disclosed, in order to determine patient compliance to the treatment regime.

US 2010/0010405 A1 discloses an apparatus and method for cyclically compressing the limb of a patient to improve blood flow in the limb. Inter alia, the use of a sensing device is disclosed which is capable of sensing a characteristic of a compression therapy performed by using the compression device.

In US 2011/0015498 A1, a system and a garment are disclosed which incorporate sensors that can be used for measuring or monitoring pressure or forces in feet, the stumps of limbs of an amputee that are fitted with prosthetic devices or any other parts of the body that are subject to forces when external pressure inducing devices are employed. Therein, one or more pressure sensors are integrally incorporated into a flexible substrate, fixed to the substrate or removably connected to the substrate.

Further, various monitoring systems are known which make use of a measurement of one or more key figures indicating patient compliance with compression therapy. As an example, US 2012/0083712 A1 discloses a monitoring system which is capable of monitoring venous refill time (VRT) via a pressure sensor in a bladder of a compression system. A controller of the compression system correlates the monitored VRT to a predetermined threshold to determine whether the patient is using the compression system.

In U.S. Pat. No. 6,231,532 B1, a method for augmenting blood circulation in the limb of a patient is provided. Again, the venous refill time of the patient is measured. The limb is wrapped with a compression sleeve having at least one pressurizable chamber. The chamber is pressurized for a predetermined period of time to compress the limb and cause blood to flow out of the limb. The chamber is depressurized until the pressure in the chamber reaches a lower value, and the chamber is closed. The pressure in the chamber is sensed and the venous refill time is determined by sensing when the pressure reaches or will reach a plateau.

In U.S. Pat. No. 7,127,370 B2, an attitude indicator device for detecting, indicating and/or logging the positional attitude of an individual in response to deviation from a set of one or more reference angles is disclosed. The device is mounted to the thigh of a patient and measurements are taken from an acceleration sensor within the device. The acceleration measurements are communicated to a receiver when the measurements deviate from acceptable thresholds, whereby the receiver indicates an alert condition.

Further, methods and devices are known which generally monitor the efficacy of compression therapy. Thus, in H. Partsch et al.: Measurement of lower leg compression in vivo: Recommendations for the performance of measurements of interface pressure and stiffness: A consensus statement, Dermatol Surg. 2006; 32: 224-233, general recommendations are provided for measuring the efficacy of compression systems by using one or more pressure sensors. Similarly, in G. Mosti et al: Comparison between a new, two-component compression system with zinc paste bandages for leg ulcer healing: a prospective, multi-center, randomized, controlled trial monitoring sub-bandage pressures, Wounds 2011; 23(5): 126-134, systems and methods for monitoring pressure exerted by compression systems are disclosed. Both documents provide an overview of different measurement techniques which may be used for determining exact pressures in compression therapy. Further, measurement routines implying resting and working pressure measurement on both legs are disclosed.

SUMMARY OF THE INVENTION

Despite the progress which has been made in compression therapy over the recent years, such as by the methods and devices disclosed in the above-mentioned documents, an ongoing need exists for devices and methods capable of effectively ensuring or assessing the efficacy of a compression device for use in compression therapy.

Specifically, this holds true with regard to precision and reproducibility of measurements, required for reliably providing current information on efficacy of compression therapy over time. Thus, specifically, due to changes and modifications in the materials of the compression systems over time and/or due to a curative effect of the compression therapy, the efficacy of the compression therapy may decrease over time, requiring attention by medical staff or the patient. Similarly, when initially applying a compression device, a precise and reliable online control is highly desirable allowing for preventing over-exerting pressure on the one hand side and providing an effective compression therapy on the other hand.

This need is fulfilled by a monitoring system, a compression system and a method for determining the efficacy of a compression device, having the features of the independent claims. Preferred embodiments of the invention, which may be realized in an isolated way or in an arbitrary combination, as the skilled person will recognize, are disclosed in the dependent claims.

As used in the following, the expressions "comprise", "include", "contain" or "have" as well as grammatical variations thereof are used in a non-exclusive way. Thus, the term "A comprises B" may refer both to the case in which A solely consists of B and to the case in which, besides B, A contains one or more further components or constituents.

In a first aspect of the present invention, a monitoring system for determining the efficacy of a compression device for use in compression therapy is disclosed. As used herein, the term efficacy may generally refer to an arbitrary parameter or combination of parameters indicative of the physical effect exerted by the compression device onto a body or body part of a user. As an example, the pressure exerted by the compression device may be a parameter or may be part of a set of parameters indicative of the efficacy.

As further used herein, the term compression therapy generally refers to an arbitrary type of therapy including exerting pressure onto a body or body part of a user such as to a limb of a user. As outlined above, compression therapy specifically may be used for curing chronic venous insufficiency (CVI) and/or any other type of disease related to CVI, such as chronic swelling of legs and ankles, ulcers and/or other diseases. However, other types of illnesses or injuries may be treated by using compression therapy, such as injuries induced by sports or accidents. Further, compression therapy may be used for preventive purposes, such as for preventing thrombosis. Thus, generally, compression therapy may be used for curative purposes as well as for preventive purposes.

As further used herein, the term compression device refers to an arbitrary device adapted for exerting pressure onto a body or body part of the user. The user, which may be a human or an animal, may also be referred to as a patient. However, the user not necessarily has to suffer from injuries and/or illnesses, since the invention may also be used for preventive purposes, such as for preventing thrombosis. The compression device, as will be outlined in further detail below, may preferably comprise one or more of a bandage, such as a flexible bandage, a sleeve, such as a flexible sleeve which may be put over a body part, specifically a limb, a garment capable of exerting pressure onto the body or a body part, or any other type of device capable of exerting pressure onto the body and/or the body part. Preferably, the compression device is capable of exerting pressure over an area of the body or body part which is at least 5 $cm^2$, more preferably at least 50 $cm^2$, more preferably at least 100 $cm^2$ and, most preferably, at least 200 $cm^2$.

As further used herein, the term monitoring system generally refers to a one-component or multicomponent device capable of determining the efficacy once or several times, preferably repeatedly over a period of time.

The monitoring system comprises the following components. The components may be combined in a single, unitary device or, alternatively, may be located decentrally and interact to form the monitoring system and to provide the functions of the monitoring system.

The monitoring system is adapted for determining the efficacy of at least one compression device for use in compression therapy, wherein the efficacy of one or more compression devices may be determined. The monitoring system comprises at least one pressure sensor for measuring a pressure exerted onto a body part of a user by the at least one compression device. As used herein, the term pressure sensor generally may refer to an arbitrary device capable of providing a signal and/or information indicative of the pressure exerted onto the body part by the compression device. Examples of pressure sensors capable of performing this type of measurement will be given in further detail below. For measuring the pressure exerted onto the body part, the pressure sensor may be located in between the compression device and the body part, such as in between the bandage and/or sleeve and the surface of the body part. Additionally or alternatively, the at least one pressure sensor may fully or partially be implemented into the compression device itself, such as by locating the pressure sensor in between several layers of the compression device, such as in between layers of a compression bandage. Again, additionally or alternatively, one or more additional layers may be interposed in between the pressure sensor and the skin of the patient, such as one or more layers of garment and/or one or more layers of tissue, which not necessarily have to be part of the compression device itself. Thus, by interposing one or more layers of tissue in between the compression device and the skin of the user, biocompatibility and/or comfort to the patient may be increased and/or the risk of inducing pain or even injuries may be reduced.

The pressure sensor may be located in one or more positions or areas in which pressure information might be of interest to the user and/or to medical staff applying the therapy to the user. Thus, one or more positions of the pressure sensor may be chosen and/or pressure sensors extending over an extended area of the compression device may be used, such as pressure sensors extending over the whole length of the compression bandage. Various options are possible.

The monitoring system further comprises at least one evaluation unit which is connectable to the pressure sensor. As used herein, the term "connectable" may both imply a situation in which a fixed and permanent connection between the evaluation unit and the pressure sensor is provided and to a situation in which both the pressure sensor and the evaluation unit each comprise at least one interface, wherein the interfaces are capable of being connected for the purpose of exchanging information. The connection between the evaluation unit and the pressure sensor, which may be a permanent connection or which may be established during use of the monitoring system, may comprise a wireless connection, such as a connection capable of exchanging information via electromagnetic radiation (such as a radio transmission and/or RF transmission), and/or a hard-wire connection, such as a connection using one or more wires, and/or a connection using one or more flexible or non-flexible tubes for exchanging gaseous and/or liquid substances and, thereby, for exchanging pressure information.

The term evaluation unit, as used herein, generally refers to an arbitrary device or combination of devices capable of evaluating one or more signals provided by the pressure sensor. The signals provided by the pressure sensor may be or may comprise one or more electronic signals, transmitted by wire and/or wirelessly, and/or may be or may comprise signals transmitted by other means, such as signals transmitted by a compression bag or compression bladder of the pressure sensor. The evaluation unit may comprise one or more data processing devices, such as one or more processors, specifically one or more microprocessors, and/or one or more integrated circuits, such as one or more application-specific integrated circuits (ASICs). The at least one evaluation unit preferably is fully or partially located outside the compression device. The pressure sensor may be partially integrated into the evaluation unit, such as by integrating an evaluation or measurement part of the pressure sensor outside the compression device and inside the evaluation unit, whereas at least one sensing portion of the pressure sensor may be located inside the compression device and/or in between the compression device and the body part of the user, for sensing the pressure. Thus, as an example, the pressure sensor may comprise a sensing portion for electronically and/or fluidically sensing the pressure exerted by the compression device, and a measuring portion connected or connectable to the sensing portion which not necessarily has to be located inside the compression device and/or in between the compression device and the body part. Thus, as an example, as will be outlined in further detail below, the pressure sensor may comprise a bladder filled with a fluid (e.g. gas and/or a liquid), which may be located in between the compression device and the body part of the user and/or inside the compression device, wherein the bladder may be compressed by the pressure exerted by the compression device. The bladder, acting as the sensing portion of the pressure sensor, may fluidically be connected to a measurement portion located outside the compression device, such as a measurement portion located inside a common casing with the at least one evaluation unit and/or inside a separate unit. Additionally or alternatively, the sensing portion of the pressure sensor may be or may comprise an electronic sensing portion, which may be located inside the compression device and/or in between the compression device and the body part, wherein the electronic sensing portion may be capable of directly and/or indirectly (such as via an optional measurement portion of the pressure sensor) transmitting pressure information to the evaluation unit.

The evaluation unit is adapted to acquire at least one resting pressure $p_{rest}$, with the user being in a resting position. As used herein, the term resting position generally refers to an arbitrary, non-upright position, in which the user may fully or partially relax, specifically in a state in which muscles of the body part to which the compression therapy is applied are relaxed. As outlined in further detail below, the resting position preferably may be a supine position, in which the user sits on a couch or lounger, with his legs in a relaxed, flexed position. For the purpose of acquiring the at least one resting pressure, the evaluation unit may provide an appropriate processor and, preferably, an appropriate software for performing a measurement routine for acquiring at least one information indicating the at least one resting pressure $p_{rest}$.

The evaluation unit is further adapted to determine at least one extended standing pressure $p_{standing, extended}$. Again, the evaluation unit may provide an appropriate measurement routine, such as by providing an appropriate software capable of running on the processor, adapted for determining the at least one extended standing pressure.

As used herein, the term extended standing pressure refers to a pressure acquired with the user being in a standing position, which is acquired to the following procedure deviating from conventional measurements of the standing pressure $p_{standing}$. As used herein, the term standing position refers to an upright position of the user, wherein the user preferably equally weights down on both legs.

As opposed to the standing pressure $p_{standing}$, which usually is measured by simply measuring the pressure at a predetermined point in time after bringing the user into the standing position, the extended standing pressure is acquired by using the following procedure:
  the evaluation unit acquires a measurement curve of pressure values after a position change of the user into the standing position; and
  a slope of the measurement curve is automatically compared to at least one endpoint threshold value and, depending on a result of the comparison, an endpoint of a change in the measurement curve induced by the position change is automatically detected and a pressure value acquired at or after the endpoint is assigned to the extended standing pressure $p_{standing, extended}$.

As used herein, the term pressure value refers to an arbitrary item or amount of information indicating a specific pressure at a specific measurement time. The term measurement curve refers to a plurality of pressure values acquired at different points in time, wherein the measurement curve additionally may comprise the measurement times of the pressure values, such as by comprising value pairs of measurements times and corresponding pressure values acquired at the specific measurement times. As outlined in further detail below, the system and the method according to the present invention may make use of a plurality of measurement curves, which may be identical or non-identical. Thereof, at least one measurement curve is used for determining the extended standing pressure. Further, as indicated in further detail below, the measurement curve may be subject to one or more filtering and/or averaging algorithms before making further use of the measurement curve, such as by averaging over a plurality of values of the measurement curve, such as 10 neighboring values of the measurement curve. In the following, no difference will be made between the use of the "raw" measurement curve, i.e. the use of the measurement curve without applying an averaging and/or filtering algorithm, and a measurement curve after applying an averaging and/or filtering algorithm, since both options are possible.

The acquisition of the measurement curve used for determining the extended standing pressure may start before, during or after the position change of the user into the standing position. The position change may take place from a generally arbitrary position being different from the standing position into the standing position, such as from a resting position into the standing position.

As further used herein, the term slope of the measurement curve generally refers to a curve indicating the increase or decrease over time of the measurement curve. Again, this curve may be subject to an averaging and/or filtering algorithm, such as by averaging over a plurality of values of the curve, such as over 10 neighboring values. In the following, no difference will be made between the use of the "raw" slope and the slope after applying an averaging and/or filtering algorithm, since both options are possible.

The slope of the measurement curve may be calculated in any way known to the skilled person. Thus, the slope may be calculated and/or derived by forming the first derivative of the measurement curve and/or by dividing a decrease and/or increase in the pressure values by the time period required for achieving this decrease or increase, respectively. Generally, for the measurement curve and/or the slope of the measurement curve, the full curves may be used or any curves derived therefrom. Thus, the measurement curve may comprise the raw values of the pressure values and/or may comprise an arbitrary curve generated by filtering and/or averaging the measurement curve, as will be outlined in further detail below. Thus, the pressure values may be acquired at a specific measurement frequency, wherein average values may be formed over a number of pressure values, such as over ten measurement values.

As used herein, the term automatically desirably refers to the fact that the evaluation unit itself is adapted to perform the specific function without the need of any user interaction. Thus, again, a software routine may be implemented in a processor of the evaluation unit which automatically compares the slope of the measurement curve to at least one endpoint threshold value. The endpoint threshold value may be stored in a data storage of the evaluation unit. Additionally or alternatively, the at least one endpoint threshold value may be modified by the user, such as by inserting the endpoint threshold value manually or via at least one electronic interface and/or via at least one human-machine-interface. Alternatively, the evaluation unit may determine the endpoint threshold value by itself. For instance, the endpoint threshold value may be derived on the basis of determined noise level during the current or earlier measurements or it could be a particular fraction of the variation of the filtered or non-filtered measured pressure values during a particular period of measuring time. The term "compare" refers to the fact that an evaluation of one or more of the following conditions takes place: Is the slope of the measurement curve above the endpoint threshold value?; Is the slope of the measurement curve above or equal the endpoint threshold value?; Is the slope of the measurement curve equal to the endpoint threshold value?; Is the slope of the measurement curve below or equal the endpoint threshold value?; Is the slope of the measurement curve below the endpoint threshold value?. A specific type of condition may be predetermined. Therein, the slope of the measurement curve may fully be evaluated and compared to the at least one endpoint threshold value, and/or a specific part of the slope of the measurement curve may be compared to the at least one endpoint threshold value. Thus, typically, a first section of the slope of the measurement curve is disregarded when comparing the slope of the measurement curve to the endpoint threshold value, in order to disregard initial steep changes of the slope of the measurement curve. Thus, a time window of several milliseconds or even several seconds may be disregarded before starting the comparison of the slope of the measurement curve and the endpoint threshold value. Examples will be given in further detail below. Instead of comparing the slope of the measurement curve to the at least one endpoint threshold value, an absolute value of the slope of the measurement curve may be compared to the endpoint threshold value, in order to disregard a negative sign of the slope of the measurement curve when comparing the slope of the measurement curve to at least one endpoint threshold value.

As opposed to the standing pressure $p_{standing}$, which, in the art, is typically acquired at a predetermined point in time or at a predetermined time span after the position change of the user into the standing position and/or at a point in time arbitrarily determined by a therapist, the extended standing pressure allows for a precise and reproducible measurement. Thus, the comparison may be performed such that the extended standing pressure $p_{standing, extended}$ is acquired at or after the endpoint, at which the slope of the measurement curve falls below a predetermined endpoint threshold value, which may indicate a significance of changes. Thus, the extended standing pressure may be measured at a point in time at which the measurement curve after the position change levels out or asymptotically approaches an endpoint value, which is more or less constant. Thus, the monitoring system as proposed, by determining the extended standing pressure $p_{standing, extended}$, is capable of providing a significant increase in reliability and reproducibility of measurement, as opposed to conventional measurements. A user interaction and/or an interaction of medical staff, introducing a non-reproducible component of arbitrariness, may be avoided by automatically detecting the endpoint of changes in the measurement curve and, thus, using the pressure value acquired at or after the endpoint, indicating an endpoint of changes in the measurement curve, as the extended standing pressure.

The monitoring system according to the present invention may generally be improved or developed further by one or more of the following preferred embodiments. Thus, firstly, the evaluation unit may be adapted to automatically acquire the measurement curve of pressure values after the position change of the user. Thus, as an example, by monitoring pressure values over time, a start of the position change may automatically be detected, indicating that the above-mentioned measurement routine for determining the extended standing pressure will have to start.

Further, the evaluation unit may be adapted to acquire the resting pressure at least once before the position change. Thus, the resting pressure $p_{rest}$ may be acquired once or several times before the start of the above-mentioned measurement routine for determining the extended standing pressure. The resting pressure may be used as a baseline for subsequent measurements.

As outlined above, the position change preferably may be a position change of the user from a resting position into the standing position. The resting position may be a sitting position and/or a supine position. However, other types of position changes are possible.

As further outlined above, the endpoint preferably may be detected automatically, by subjecting the slope of the measurement curve to one or more conditions implying the at least one endpoint threshold value. Preferably, the at least one endpoint threshold value indicates an upper limit of tolerable changes of the measurement curve, below which the measurement curve is considered to be stable and/or is considered to have reached its asymptotic end value. Thus, preferably, the endpoint is automatically detected when the slope of the measurement curve is equal or below the endpoint threshold value.

The endpoint threshold value, specifically in the case this endpoint threshold value indicates a maximum tolerable change in the measurement curve, preferably may be a change in the measurement curve over time is equal to or less than 1 mmHg per second, preferably equal to or less than 0.2 mmHg per second, more preferably equal to or less than 0.05 mmHg per second. However, other types of endpoint threshold values may be used alternatively and/or in addition.

As outlined above, the measurement curve and/or the slope of the measurement curve may be subject to at least one averaging and/or at least one filtering algorithm. The evaluation unit may be adapted to perform this averaging and/or filtering algorithm. Thus, preferably, the evaluation unit may be adapted to perform at least one of an averaging operation and at least one filtering operation on the measurement curve before comparing the slope of the measurement curve to the endpoint threshold value. As an example, an averaging operation may be used which generates a median over a predetermined number of pressure values, preferably over 3 to 20 pressure values, more preferably over 5 to 15 pressure values and most preferably over 10 pressure values. However, additionally or alternatively to generating a median, other types of averaging operations may be used, such as an averaging operation which generates a geometric mean and/or an arithmetic mean value.

The evaluation unit generally may be adapted to determine at least one key figure by using pressure values provided by the pressure sensor. As used herein, the term key figure generally refers to an arbitrary measure of efficacy of the compression system. Thus, the at least one key figure may directly or indirectly imply one or more types of information derived directly or indirectly from the pressure values, such as one or more pieces of information indicating the pressure exerted by the compression device onto the body part of the user. Additionally, the at least one key figure may directly or indirectly be indicative of one or more physiological parameters and/or body functions which are directly or indirectly linked to the compression therapy and/or the pressure exerted onto the body of the user by the compression device. Examples of key figures which may directly or indirectly be determined by using pressure values provided by the pressure sensor will be given in more details below.

Generally, the evaluation unit may be adapted to compare the key figure K to at least one efficacy threshold, such as a predetermined efficacy threshold and/or at least one efficacy threshold which may be provided by a user of the monitoring system, for automatically determining the efficacy of the compression device.

When using one or more key figures for determining the efficacy of the compression system, preferably, a plurality of different key figures may be used. Thus, specifically, the evaluation unit may be adapted to determine at least two different key figures $K_1$ and $K_2$. The evaluation unit may be adapted to automatically determine the efficacy of the compression device by a combination of the at least two key figures $K_1$ and $K_2$. Thus, the combination of the key figures $K_1$ and $K_2$ may generally comprise an arbitrary combination of these key figures and/or of one or more figures derived from these key figures $K_1$, $K_2$. Specifically, the evaluation unit may be adapted to perform at least one multivariate evaluation operation $f(K_1,K_2)$ using the key figures $K_1$ and $K_2$, wherein the evaluation operation is adapted to generate a statement on the efficacy of the compression device. As an example, a linear combination of $K_1$ and $K_2$ and, optionally, other key figures may be used.

The at least one key figure preferably may be selected from the group consisting of:
the resting pressure $p_{rest}$;
a standing pressure $p_{standing}$ with the user being in a standing position;
a baseline resting pressure $p_{rest,\ baseline}$ directly after application of the compression system;
the extended standing pressure $p_{standing,\ extended}$;
a static stiffness index SSI, the static stiffness index being determined by subtracting the resting pressure $p_{rest}$ from a standing pressure $p_{standing}$;
an extended static stiffness index ESSI, the extended static stiffness index being determined by subtracting the resting pressure $p_{rest}$ from the extended standing pressure $p_{standing,\ extended}$;
a difference $ESSI_1-ESSI_2$ between at least two extended static stiffness indices $ESSI_1$ and $ESSI_2$, the extended static stiffness index $ESSI_1$ being determined by subtracting a first resting pressure $p_{rest1}$ from a first extended standing pressure $p_{standing,\ extended\ 1}$, the extended static stiffness index $ESSI_2$ being determined by subtracting a second resting pressure $p_{rest2}$ from a second extended standing pressure $p_{standing,\ extended\ 2}$;
a difference $SSI_1-SSI_2$ between at least two static stiffness indices $SSI_1$ and $SSI_2$, the static stiffness index $SSI_1$ being determined by subtracting a first resting pressure $p_{rest1}$ from a first standing pressure $p_{standing1}$, the static stiffness index $SSI_2$ being determined by subtracting a second resting pressure $p_{rest2}$ from a second standing pressure $p_{standing2}$;
a ratio $ESSI_1:ESSI_2$ of at least two extended static stiffness indices $ESSI_1$ and $ESSI_2$, the extended static stiffness index $ESSI_1$ being determined by subtracting a first resting pressure $p_{rest1}$ from a first extended standing pressure $p_{standing,\ extended\ 1}$, the extended static stiffness index $ESSI_2$ being determined by subtracting a second resting pressure $p_{rest2}$ from a second extended standing pressure $p_{standing,\ extended\ 2}$;
a ratio $SSI_1:SSI_2$ of at least two static stiffness indices $SSI_1$ and $SSI_2$, the static stiffness index $SSI_1$ being determined by subtracting a first resting pressure $p_{rest1}$ from a first standing pressure $p_{standing1}$, the static stiffness index $SSI_2$ being determined by subtracting a second resting pressure $p_{rest2}$ from a second standing pressure $p_{standing2}$;
a difference between at least two resting pressures $p_{rest1}$ and $p_{rest2}$ acquired at at least two different points in time;
a ratio between at least two resting pressures $p_{rest1}$ and $p_{rest2}$ acquired at at least two different points in time;
a difference between at least two extended standing pressures $p_{standing,\ extended\ 1}$ and $p_{standing,\ extended\ 2}$ acquired at at least two different points in time;
a difference between at least two standing pressures $p_{standing1}$ and $p_{standing2}$ acquired at at least two different points in time;
a ratio of at least two extended standing pressures $p_{standing,\ extended\ 1}$ and $p_{standing,\ extended\ 2}$ acquired at at least two different points in time;
a ratio of at least two standing pressures $p_{standing1}$ and $p_{standing2}$ acquired at at least two different points in time;
an median or mean amplitude of a measurement curve of pressure values acquired during a defined movement of the user, preferably during walking;
a ratio of at least one first median or mean amplitude ($Amplitude_{median1}$ or $Amplitude_{mean1}$) of a first measurement curve of pressure values acquired during a first defined movement of the user (e.g. during a first period of walking) and at least one second median or mean amplitude ($\text{Amplitude}_{median2}$ or $\text{Amplitude}_{mean2}$) of a second measurement curve of pressure values acquired during a second defined movement of the user (e.g. during a second period of walking);

a refilling time $t_{refill}$ for vein refilling after a change of position from a resting position into a standing position;

a difference $t_{refill1}-t_{refill2}$ between at least one first refilling time $t_{refill1}$ for vein refilling after a first change of position from a resting position into a standing position and at least one second refilling time $t_{refill2}$ for vein refilling after a first change of position from a resting position into a standing position;

a ratio $t_{refill1}:t_{refill2}$ of at least one first refilling time $t_{refill1}$ for vein refilling after a first change of position from a resting position into a standing position and at least one second refilling time $t_{refill2}$ for vein refilling after a first change of position from a resting position into a standing position;

a parameter derived from a refilling curve, the refilling curve being a measurement curve acquired after a change of position from a resting position into a standing position, specifically a parameter indicating at least one of a slope of the refilling curve and a shape of the refilling curve.

The resting pressure, the standing pressure and the extended standing pressure have been discussed in detail above. The baseline resting pressure $p_{rest,\, baseline}$ generally is a resting pressure $p_{rest}$ measured directly after application of the compression system, such as within a time span of less than about 30 minutes after application of the compression system and allowing the compression system and/or the pressure sensor to settle, for example after the patient has freely moved around or has stood up at least once. While typically the resting pressure will be determined prior to standing pressure, it will be appreciated that it is possible to alternate the sequence, where standing pressure is determined prior to resting pressure.

The extended static stiffness index ESSI is a new key figure which makes use of the extended standing pressure $p_{standing,\, extended}$. Thus, as compared to the conventional static stiffness index SSI, the extended static stiffness index is a more reliable key figure. Similarly, the difference between two different extended static stiffness indices $\text{ESSI}_1$ and $\text{ESSI}_2$ is more reliable than the conventional difference $\text{SSI}_1-\text{SSI}_2$. Again, similarly, the ratio $\text{ESSI}_1:\text{ESSI}_2$ is a more reliable and more reproducible key figure as compared to $\text{SSI}_1:\text{SSI}_2$. However, the conventional key figures SSI, $\text{SS}_1$, and $\text{SSI}_2$ may be used additionally or alternatively.

Further details regarding conventional measurements of the static stiffness index SSI are explained in the above-mentioned publication by H. Partsch et al.

As outlined above, each of the key figures and/or an arbitrary combination of the key figures may be compared to at least one efficacy threshold, such as for automatically determining the efficacy of the compression system. Exemplary embodiments of efficacy thresholds, which may be used within the present invention, will be given in further detail below.

The evaluation unit generally may be adapted to invite the user to perform at least one measurement routine for measuring the at least one key figure. Thus, the monitoring system may provide one or more optical and/or acoustical signals to the user to indicate that performing a specific measurement routine is advisable and/or indicating specific steps to be taken by the user in order to perform the measurement routine. Thus, as will be outlined in detail below, the evaluation unit may provide one or more display devices and/or acoustic output devices such as loudspeakers, allowing for an interaction with the user and allowing for indicating to the user the steps to be taken for performing the measurement routine.

The evaluation unit further may be adapted to generate at least one warning in case the key figure is detected to be outside an admissible range. Thus, one or more of the key figures or an arbitrary combination of the key figures may be compared to one or more thresholds indicating an admissible range for the respective key figures and/or combination of key figures. Thus, a warning may be generated in case a specific key figure is detected to be too high or too low. The at least one admissibility threshold may be predetermined and/or may be adaptable or determinable by the at least one user and/or by a medical staff. The at least one warning may be an acoustic and/or a visual and/or a haptic warning which may be output to the user, such as by visual indicia provided on a display device and/or a warning sound. Additionally or alternatively, an electronic warning may be generated, such as by providing an appropriate warning signal to another device, such as a patient monitoring system which is connected to the monitoring system. Thus, the monitoring system may be implemented into and/or may be part of a general medical system for patient care.

The monitoring system, as outlined above, preferably may comprise one or more user interfaces, allowing for providing information to the user and/or allowing for the user to input commands and/or information. Thus, the monitoring system may comprise at least one display element, and the evaluation unit preferably is adapted to provide instructions to the user via the display element. Thus, the evaluation unit may be adapted to provide instructions to the user which position to take. Additionally or alternatively, the display element may be adapted to output specific measurement information, such as one or more pressure values and/or one or more of the above mentioned key figures.

The monitoring system may further be adapted to lead the user through at least one measurement routine. Thus, as outlined above, the monitoring system, preferably the evaluation unit, may be adapted to provide acoustic and/or visual and/or haptic instructions to the user in order to indicate to the user which steps to take for performing the measurement routine. Thus, specific instructions regarding a position to be taken by the user may be provided. As an example, the user, in the measurement routine, may at least once take the resting position, wherein the resting pressure $p_{rest}$ is acquired at least once by the monitoring system. Further, in the measurement routine, the user at least once may take the standing position, wherein, in the standing position, the standing pressure $p_{standing}$ and/or the extended standing pressure $p_{standing,\, extended}$ are determined at least once.

As outlined above, the resting position preferably is a supine position. As used herein, the term supine refers to a dorsal position in which the user rests on a couch or lounger with his back, preferably with his knees flexed and his feet supported by the couch or lounger, respectively. Preferably, the legs are in a relaxed position.

The monitoring system, preferably the evaluation unit, may further be adapted to recognize at least one predetermined type of movement of the user by evaluating a measurement curve of pressure values. The measurement curve of pressure values may be the same as the measurement curve of pressure values used for the extended standing pressure $p_{standing,\, extended}$. Alternatively, a different measurement curve may be used. Thus, preferably, the evaluation unit may be adapted for determining a walking movement of the user by recognizing period changes of the pressure values in the measurement curve of pressure values. Further, the evaluation unit may be adapted to store an activity profile of the user. Thus, as used herein, the term activity profile of the user refers to an arbitrary amount of data indicating activity-induced pressure values or changes of pressure values, such as activity profiles determined or generated by walking movement and/or sports. The evaluation unit may further be adapted to use a pattern recognition algorithm for comparing a measurement curve of pressure values to a predetermined set of reference patterns.

Again, the measurement curve of pressure values may be the same measurement curve of pressure values as used above for the purpose of determining the extended standing pressure $p_{standing,\ extended}$ and/or the measurement curve of pressure values as used above for recognizing at least one predetermined type of movement of the user. Additionally or alternatively, at least one separate measurement curve of pressure values may be used. As further used herein, the term reference pattern refers to a specific section of a measurement curve which may be stored in a data storage of the evaluation unit and which may indicate a specific type of activity of the user and/or which may indicate a specific physiological state of the user. Thus, by comparing the measurement curve to a predetermined set of reference patterns, a specific activity may be detected, such as a walking movement and/or any other type of predetermined activity. Additionally or alternatively, by comparing the measurement curve of pressure values to a predetermined set of reference patterns, one or more illnesses may be detected.

Further preferred embodiments may refer to the type of pressure sensor. As indicated above, the pressure sensor itself may comprise at least one sensing element and/or at least one sensing portion. Additionally and optionally, the pressure sensor may comprise at least one further portion, such as at least one evaluation portion and/or measurement portion. The pressure sensor preferably may be selected from the group consisting of: a semiconductor pressure sensor; a pressure sensor having a deformation-sensitive resistor; a pressure sensor having a deformation-sensitive capacitor; a pressure sensor having a deformation-sensitive light guide; a pressure sensor having a fluid-filled bladder. In the latter case, the fluid-filled bladder may be the sensing portion of the pressure sensor, whereas at least one pressure transducer may be connected to the bladder fluidically, such as by at least one tube.

In a further preferred embodiment, the evaluation unit may be adapted to detect arterial pulsations in a measurement curve of pressure values provided by the pressure sensor. Again, the measurement curve of pressure values may be identical to one or more of the measurement curves disclosed above used for different purposes. Again, additionally or alternatively, a separate measurement curve may be used for detecting the arterial pulsations. For detecting the arterial pulsations, a frequency-based analysis of the measurement curve may be performed, such as a Fourier transformation. Additionally or alternatively, a filtering algorithm may be used, such as by filtering periodic pulsations in the measurement curve in a typical range of frequencies for arterial pulsations, such as in a range of 30 beats per minute to 200 beats per minute. The evaluation unit may further be adapted to generate a warning in case an amplitude of the arterial pulsations is below a predetermined safety threshold. Thus, again, an acoustic warning and/or a visual warning and/or a haptic warning and/or an electronic warning may be generated in case the amplitude of the arterial pulsations is below the predetermined safety threshold. The warning may indicate to the user or to the medical staff that the person is in a critical condition and/or that the compression device exerts an overpressure onto the body part of the user.

As outlined above, the evaluation unit preferably may comprise at least one processor. The at least one processor generally may include an arbitrary type of data evaluation device, including a microprocessor and/or a volatile or non-volatile data storage. Further, one or more electronic interfaces and/or one or more user interfaces may be comprised.

In a further aspect of the present invention, a compression system for use in compression therapy is disclosed. The compression system comprises at least one monitoring system according to one or more of the embodiments disclosed above or according to one or more of the embodiments disclosed in further detail below. The compression system further comprises at least one compression device for exerting pressure onto a body part of a user.

As outlined above, the compression device preferably comprises at least one of: a compression bandage, a compression sleeve, a compression garment. Additionally or alternatively, other types of compression devices may be used. Most preferably, the compression device comprises at least one textile material such as at least one cloth and/or fabric and/or fiber material. Most preferably, the compression device comprises at least one flexible or elastic material, preferably having a specific stiffness.

Further, the compression device preferably is a passive compression device. As used herein, the term passive compression device refers to a device which is capable of exerting the pressure onto the body part of the user due to its elastic or flexible properties, in conjunction with a predetermined elongation and/or expansion of the compression device prior to application or during application. Thus, the passive compression device preferably is a compression device which does not include any type of actuator, such as a hydraulic or electric actuator.

As outlined above, the body part generally may be or may comprise an arbitrary part of the body of the user. Thus, the body part preferably may be selected from the group consisting of: a leg of the user or a part of a leg of the user; a calf of the user; a thigh of the user; an arm of the user or a part of an arm of the user such as a forearm or an upper arm of the user; a finger or a finger digit of the user; a toe of the user; a foot of the user or a part of a foot of the user. Additionally or alternatively, other anatomical areas may be used for the compression therapy, in which compression and pressure measurements may be appropriate.

In a further aspect of the present invention, a method for determining the efficacy of at least one compression device for use in compression therapy is disclosed. The method preferably may make use of the monitoring system and/or the compression system as disclosed in one or more of the embodiments listed above or listed in further detail below. Thus, for specific embodiments of the method, reference may be made to the monitoring system and/or the compression system. However, other types of devices may be used.

In the method, at least one pressure sensor is used for measuring a pressure exerted onto a body part of a user by the compression device. Therein, at least one resting pressure $p_{rest}$ with the user being in a resting position is acquired. Further, at least one extended standing pressure $p_{standing,\ extended}$ with the user being in a standing position is determined, by using the following procedure:

a measurement curve of pressure values after a position change of the user into the standing position is acquired;

a slope of the measurement curve is automatically compared to at least one endpoint threshold value and, depending on a result of the comparison, an endpoint of a change in the measurement curve induced by the position change is automatically detected, and a pressure value acquired at or after the endpoint is assigned to the extended standing pressure $p_{standing,\ extended}$.

For further details and optional embodiments of the method, reference may be made to the disclosure of the monitoring system and/or the compression system above or below. Thus, again, the method may imply the determination of one or more key figures, as outlined above. Again, one or more of the key figures may be compared to one or more threshold values, such as to one or more safety threshold values. Again, a warning may be created in case one or more of the key figures may be too high or too low or out of range, such as in case the pressure exerted onto the body part is too high. Thus, appropriate warnings for excessive pressures such as baseline pressures, resting pressures, standing pressures, extended standing pressures and so on may be generated.

As an example, a normal range for the resting pressure $p_{rest}$ may be 10 to 70 mmHg, preferably 20 to 50 mmHg and, most preferably 25 to 35 mmHg. In case the resting pressure is outside the named range, a warning may be created.

Additionally or alternatively, the standing pressure $p_{standing}$ and/or the extended standing pressure $p_{standing,\ extended}$, may be compared to one or more limit values. Thus, an admissible range for these standing pressures or extended standing pressures may be 30 to 120 mmHg, more preferably 40 to 100 mmHg and, most preferably, 45 mmHg to 65 mmHg.

Typically the time period needed to make an ESSI measurement depends on the particular patient's condition. For example for a patient having a severe venous insufficiency a measurement of ESSI may be completed in a short period e.g. as low as 30 seconds or even less, whereas a ESSI measurement for a healthy patient requires a longer period, e.g. up to 3 minutes.

As outlined above, the method preferably may use the monitoring system according to one or more of the embodiments disclosed above and/or according to one or more of the embodiments disclosed in further detail below. Thus, in case the evaluation unit is disclosed to be adapted to perform a specific action, the method may imply an appropriate method step. Similarly, the monitoring system and/or the compression system may be adapted to perform a method according to the present invention.

As outlined above, the method preferably may be performed such that at least one key figure K is determined by using pressure values provided by the pressure sensor. The at least one key figure preferably may be a measure of efficacy of the compression device. As outlined above, the key figure preferably may be compared to one or more threshold values, such as to one or more predetermined threshold values. Most preferably, the compression device may be exchanged in case the compression device's efficacy is found to be below a predetermined threshold, such as in case a predetermined key figure is found to be out of range.

Summarizing the above-mentioned findings, the following embodiments are preferred:

Embodiment 1: A monitoring system for determining the efficacy of at least one compression device for use in compression therapy, the monitoring system comprising:

at least one pressure sensor for measuring a pressure exerted onto a body part of a user by the compression device; and at least one evaluation unit which is connectable to the pressure sensor;

wherein the evaluation unit is adapted to acquire at least one resting pressure $p_{rest}$ with the user being in a resting position, wherein the evaluation unit is further adapted to determine at least one extended standing pressure $p_{standing,\ extended}$ with the user being in a standing position, by using the following procedure:

the evaluation unit acquires a measurement curve of pressure values after a position change of the user into the standing position;

a slope of the measurement curve is automatically compared to at least one endpoint threshold value and, depending on a result of the comparison, an endpoint of a change in the measurement curve induced by the position change is automatically detected, and a pressure value acquired at or after the endpoint is assigned to the extended standing pressure $p_{standing,\ extended}$.

Embodiment 2: The monitoring system according to the preceding embodiment, wherein the evaluation unit is adapted to automatically acquire the measurement curve of pressure values after the position change of the user.

Embodiment 3: The monitoring system according to one of the preceding embodiments, wherein the evaluation unit is adapted to acquire the resting pressure $p_{rest}$ at least once before the position change or at least once after the position change.

Embodiment 4: The monitoring system according to one of the preceding embodiments, wherein the position change is a position change of the user from a resting position into the standing position.

Embodiment 5: The monitoring system according to one of the preceding embodiments, wherein the endpoint is automatically detected when the slope of the measurement curve is equal or below the endpoint threshold value.

Embodiment 6: The monitoring system according to one of the preceding embodiments, wherein the endpoint threshold value is a change in the measurement curve of equal to or less than 1 mmHg per second, preferably equal to or less than 0.2 mmHg per second, more preferably equal to or less than 0.05 mmHg per second.

Embodiment 7: The monitoring system according to one of the preceding embodiments, wherein the evaluation unit is adapted to perform at least one of an averaging operation and a filtering operation on the measurement curve before comparing the slope of the measurement curve to the endpoint threshold value.

Embodiment 8: The monitoring system according to the preceding embodiment, wherein an averaging operation is used which generates a median over a predetermined number of pressure values, preferably over 3-20 pressure values, more preferably over 5-15 pressure values and most preferably over 10 pressure values.

Embodiment 9: The monitoring system according to one of the preceding embodiments, wherein the evaluation unit is adapted to determine at least one key figure K by using pressure values provided by the pressure sensor, wherein the at least one key figure is a measure of the efficacy of the compression system.

Embodiment 10: The monitoring system according to the preceding embodiment, wherein the evaluation unit is adapted to compare the key figure K to at least one efficacy threshold for automatically determining the efficacy of the compression device.

Embodiment 11: The monitoring system according to one of the two preceding embodiments, wherein the evaluation unit is adapted to determine at least two different key figures K1 and K2, wherein the evaluation unit is adapted to automatically determine the efficacy of the compression device by a combination of the at least two key figures K1 and K2.

Embodiment 12: The monitoring system according to the preceding embodiment, wherein the evaluation unit is adapted to perform at least one multivariate evaluation operation f(K1, K2) using the key figures K1 and K2, the evaluation operation being adapted to generate a statement on the efficacy of the compression device.

Embodiment 13: The monitoring system according to one of the four preceding embodiments, wherein the key figure is selected from the group consisting of:

the resting pressure $p_{rest}$;

a standing pressure $p_{standing}$ with the user being in a standing position;

a baseline resting pressure $p_{rest,\ baseline}$ directly after application of the compression system;

the extended standing pressure $p_{standing,\ extended}$;

a static stiffness index SSI, the static stiffness index being determined by subtracting the resting pressure $p_{rest}$ from a standing pressure $p_{standing}$;

an extended static stiffness index ESSI, the extended static stiffness index being determined by subtracting the resting pressure $p_{rest}$ from the extended standing pressure $p_{standing,\ extended}$;

a difference ESSI1−ESSI2 between at least two extended static stiffness indices ESSI1 and ESSI2, the extended static stiffness index ESSI1 being determined by subtracting a first resting pressure $p_{rest1}$ from a first extended standing pressure $p_{standing,\ extended\ 1}$, the extended static stiffness index ESSI2 being determined by subtracting a second resting pressure $p_{rest2}$ from a second extended standing pressure $p_{standing,\ extended\ 2}$;

a difference SSI1−SSI2 between at least two static stiffness indices SSI1 and SSI2, the static stiffness index SSI1 being determined by subtracting a first resting pressure $p_{rest1}$ from a first standing pressure $p_{standing1}$, the static stiffness index SSI2 being determined by subtracting a second resting pressure $p_{rest2}$ from a second standing pressure $p_{standing2}$;

a ratio ESSI1:ESSI2 of at least two extended static stiffness indices ESSI1 and ESSI2, the extended static stiffness index ESSI1 being determined by subtracting a first resting pressure $p_{rest1}$ from a first extended standing pressure $p_{standing,\ extended\ 1}$, the extended static stiffness index ESSI2 being determined by subtracting a second resting pressure $p_{rest2}$ from a second extended standing pressure $p_{standing,\ extended\ 2}$;

a ratio SSI1:SSI2 of at least two static stiffness indices SSI1 and SSI2, the static stiffness index SSI1 being determined by subtracting a first resting pressure $p_{rest1}$ from a first standing pressure $p_{standing1}$, the static stiffness index SSI2 being determined by subtracting a second resting pressure $p_{rest2}$ from a second standing pressure $p_{standing2}$;

a difference between at least two resting pressures $p_{rest1}$ and $p_{rest2}$ acquired at at least two different points in time;

a ratio between at least two resting pressures $p_{rest1}$ and $p_{rest2}$ acquired at at least two different points in time;

a difference between at least two extended standing pressures $p_{standing,\ extended\ 1}$ and $p_{standing,\ extended\ 2}$ acquired at at least two different points in time;

a difference between at least two standing pressures $p_{standing1}$ and $p_{standing2}$ acquired at at least two different points in time;

a ratio of at least two extended standing pressures $p_{standing,\ extended\ 1}$ and $p_{standing,\ extended\ 2}$ acquired at at least two different points in time;

a ratio of at least two standing pressures $p_{standing1}$ and $p_{standing2}$ acquired at at least two different points in time;

an median or mean amplitude of a measurement curve of pressure values acquired during a defined movement of the user, preferably during walking;

a ratio of at least one first median or mean amplitude (Amplitude$_{median1}$ or Amplitude$_{mean1}$) of a first measurement curve of pressure values acquired during a first defined movement of the user (e.g. during a first period of walking) and at least one second median or mean amplitude (Amplitude$_{median2}$ or Amplitude$_{mean2}$) of a second measurement curve of pressure values acquired during a second defined movement of the user (e.g. during a second period of walking);

a refilling time $t_{refill}$ for vein refilling after a change of position from a resting position into a standing position;

a difference $t_{refill1}-t_{refill2}$ between at least one first refilling time $t_{refill1}$ for vein refilling after a first change of position from a resting position into a standing position and at least one second refilling time $t_{refill2}$ for vein refilling after a first change of position from a resting position into a standing position;

a ratio $t_{refill1}:t_{refill2}$ of at least one first refilling time $t_{refill1}$ for vein refilling after a first change of position from a resting position into a standing position and at least one second refilling time $t_{refill2}$ for vein refilling after a first change of position from a resting position into a standing position;

a parameter derived from a refilling curve, the refilling curve being a measurement curve acquired after a change of position from a resting position into a standing position, specifically a parameter indicating at least one of a slope of the refilling curve and a shape of the refilling curve.

Embodiment 14: The monitoring system according to one of the five preceding embodiments, wherein the evaluation unit is adapted to invite the user to perform at least one measurement routine for measuring the at least one key figure.

Embodiment 15: The monitoring system according to one of the six preceding embodiments, wherein the evaluation unit is adapted to generate a warning in case the key figure is detected to be outside an admissible range.

Embodiment 16: The monitoring system according to one of the preceding embodiments, wherein the monitoring system comprises at least one display element.

Embodiment 17: The monitoring system as claimed in the preceding embodiment, wherein the evaluation unit is adapted to provide instructions to the user which position to take, via the display element.

Embodiment 18: The monitoring system according to one of the preceding embodiments, wherein the monitoring system is adapted to lead the user through at least one measurement routine.

Embodiment 19: The monitoring system according to the preceding embodiment, wherein the user, in the measurement routine, at least once takes the resting position and the resting pressure $p_{rest}$ is acquired at least once by the monitoring system, and wherein the user, in the measurement routine, at least once takes the standing position and the standing pressure $p_{standing}$ and/or the extended standing pressure $p_{standing, extended}$ are determined at least once.

Embodiment 20: The monitoring system according to one of the preceding embodiments, wherein the resting position is a supine position.

Embodiment 21: The monitoring system according to one of the preceding embodiments, wherein the evaluation unit is adapted to recognize at least one predetermined type of movement of the user by evaluating a measurement curve of pressure values.

Embodiment 22: The monitoring system according to one of the preceding embodiments, wherein the evaluation unit is adapted for determining a walking movement of the user by recognizing periodic changes of the pressure values.

Embodiment 23: The monitoring system according to one of the preceding embodiments, wherein the evaluation unit is adapted to store an activity profile of the user.

Embodiment 24: The monitoring system according to one of the preceding embodiments, wherein the evaluation unit is adapted to use a pattern recognition algorithm for comparing a measurement curve of pressure values to a predetermined set of reference patterns.

Embodiment 25: The monitoring system according to one of the preceding embodiments, wherein the pressure sensor is selected from the group consisting of: a semiconductor pressure sensor; a pressure sensor having a deformation-sensitive resistor; a pressure sensor having a deformation-sensitive capacitor; a pressure sensor having a deformation-sensitive light guide; and a pressure sensor having a fluid-filled bladder.

Embodiment 26: The monitoring system according to one of the preceding embodiments, wherein the evaluation unit is adapted to detect arterial pulsations in a measurement curve of pressure values provided by the pressure sensor.

Embodiment 27: The monitoring system according to the preceding embodiment, wherein the evaluation unit is further adapted to generate a warning in case an amplitude of the arterial pulsations is below a predetermined safety threshold.

Embodiment 28: The monitoring system according to one of the preceding embodiments, wherein the evaluation unit comprises at least one processor.

Embodiment 29: A compression system for use in compression therapy, the compression system comprising at least one monitoring system according to one of the preceding embodiments, the compression system further comprising at least one compression device for exerting pressure onto a body part of a user.

Embodiment 30: The compression system according to the preceding embodiment, wherein the compression device comprises at least one of: a compression bandage; a compression sleeve; a compression garment.

Embodiment 31: The compression system according to one of the two preceding embodiments, wherein the compression device is a passive compression device.

Embodiment 32: The compression system according to one of the three preceding embodiments, wherein the body part is selected from the group consisting of: a leg of the user or a part of a leg of the user; a calf of the user; a thigh of the user; an arm of the user or a part of an arm of the user; a finger or a finger digit of the user; a toe of the user; a foot of the user or a part of a foot of the user.

Embodiment 33: A method for determining the efficacy of at least one compression device for use in compression therapy, wherein at least one pressure sensor is used for measuring a pressure exerted onto a body part of a user by the compression device, wherein at least one resting pressure $p_{rest}$ with the user being in a resting position is acquired, wherein further at least one extended standing pressure $p_{standing, extended}$ with the user being in a standing position is determined, by using the following procedure:

a measurement curve of pressure values after a position change of the user into the standing position is acquired;

a slope of the measurement curve is automatically compared to at least one endpoint threshold value and, depending on a result of the comparison, an endpoint of a change in the measurement curve induced by the position change is automatically detected, and a pressure value acquired at or after the endpoint is assigned to the extended standing pressure $p_{standing, extended}$.

Embodiment 34: The method according to the preceding embodiment, wherein the method uses the monitoring system according to one of the preceding embodiments referring to a monitoring system.

Embodiment 35: The method according to one of the two preceding embodiments, wherein at least one key figure K is determined by using pressure values provided by the pressure sensor, wherein the at least one key figure is a measure of the efficacy of the compression device.

Embodiment 36: The method according to one of the two preceding embodiments, wherein the compression device is exchanged in case the compression device's efficacy is found to be below a predetermined threshold.

SHORT DESCRIPTION OF THE FIGURES

Further details of the invention may be derived from the following disclosure of preferred embodiments.

The features of the embodiments may be realized in an isolated way or in any combination. The invention is not restricted to the embodiments. The embodiments are schematically depicted in the figures. Identical reference numbers in the figures refer to identical elements or functionally identical elements or elements corresponding to each other with regard to their functions.

DETAILED DESCRIPTION

Figure 1:
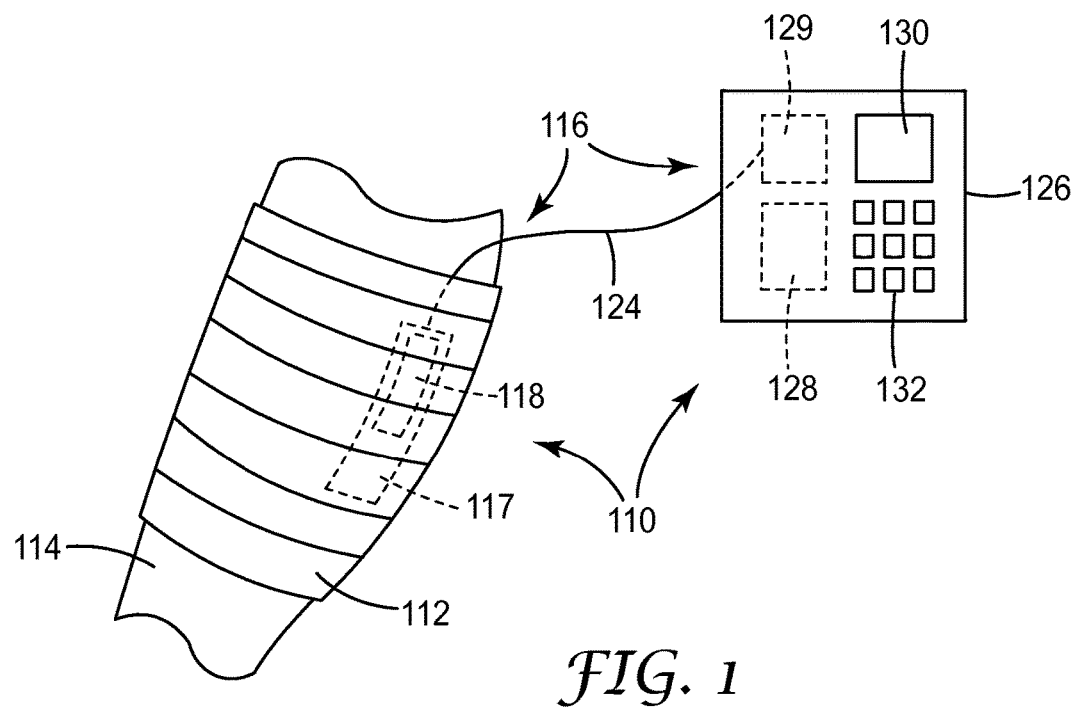
FIG. 1 shows an exemplary embodiment of a compression system and a monitoring system.

In FIG. 1, an exemplary embodiment of a monitoring system 116 for determining the efficacy of a compression device used for exerting pressure onto a body part of a user in the framework of compression therapy as well as an exemplary compression system 110 for use in compression therapy is depicted. The compression system 110 comprises at least one monitoring system 116 and at least one compression device 112 for exerting pressure onto a body part 114 of a user, such as a calf. The compression device 112, as depicted in FIG. 1, preferably may comprise a compression bandage. However, other types of compression devices may be used additionally or alternatively.

As shown in FIG. 1, the monitoring system 116 typically comprises at least two units: a sensing unit 117 and an evaluation unit 126. The sensing unit 117 may be placed in between the compression device 112 and the body part 114 of the compression device user and/or may be placed fully or partially inside the compression device 112, such as between two or more layers of the compression bandage. The evaluation unit 126 is typically to be located outside of the compression device e.g. for ease in viewing and handling by the user or others (e.g. medical personnel). Typically said units are connected or connectable e.g. by one or more wireless or hard (e.g. wire) connection as indicated in FIG. 1 via the line labeled with reference number 124.

Sensing unit 117 may comprises a pressure sensor 118 for measuring a pressure exerted onto the body part 114 by the compression device 112 as shown in exemplary embodiment of FIG. 1. For pressure sensors comprising a sensing portion/element (120, not shown in FIG. 1) and evaluation/measurement portion (122, not shown in FIG. 1) for example pressure sensors comprising a fluid-filled bladder, in alternative embodiments, the sensing unit may comprise the sensing portion/element of such a pressure sensor, where the evaluation/measuring portion of such a pressure sensor may be then located in another part of the monitoring system (for example in the evaluation unit) and where the sensing and measurement portions of the pressure sensor may be then connected by at least one connection. The at least one evaluation unit is typically connectable to the pressure sensor, i.e. to the pressure sensor per se or to an appropriate portion of the pressure sensor.

The evaluation unit 126 preferably may comprise one or more processors 128, such as one or more microprocessors. Additionally, the evaluation unit 126 may comprise one or more data storage devices 129, such as one or more volatile and/or non-volatile data storage devices.

The evaluation unit 126 may further comprise one or more user interfaces and/or one or more electronic interfaces, such as one or more data interfaces. Thus, as indicated in FIG. 1, the evaluation unit 126 may comprise one or more display elements 130, such as one or more segmented displays and/or one or more matrix displays. Further, one or more keypads 132 and/or other types of input devices allowing for a user to input data and/or commands into the evaluation unit 126 may be comprised.

The evaluation unit 126 preferably is adapted to perform a method for determining the efficacy of the compression device 112. As outlined above, the evaluation unit 126 is adapted to acquire at least one resting pressure $p_{rest}$ with the user being in a resting position. The evaluation unit 126 is further adapted to determine at least one extended standing pressure $p_{standing,\,extended}$ with the user being in a standing position, by using the following procedure:
the evaluation unit 112 acquires a measurement curve of pressure values after a position change of the user into the standing position;
a slope of the measurement curve is automatically compared to at least one endpoint threshold value and, depending on a result of the comparison, an endpoint of a change in the measurement curve induced by the position change is automatically detected, and a pressure value acquired at or after the endpoint is assigned to the extended standing pressure $p_{standing,\,extended}$.

In the following, several embodiments of the method are disclosed which are suited to assess if the compression system 110 and, specifically, the compression device 112, are effective. Initial efficacy may be measured directly after application of the compression system 110 (baseline measurement).

In the following, pressures, key figures or time-related data determined during initial measurement will be indexed with a "1". The system may store baseline measurements of a patient together with user-specific information, such as a specific RFID ID-code assigned to the compression device 112 and/or the pressure sensor 118.

After hours or days it may be expected that compression properties of the compression device 112 change, potentially resulting in therapeutically inefficacy. Time, pressure data and key figures determined after some time of wearing will be indexed with a "2". Via RFID ID-code one or more consecutive values may be compared with baseline data.

According to current medical standard, typically, sub-bandage pressures and key figures are used as a surrogate marker for bandage efficacy, also called bandage efficacy. However, these pressure values are measured manually. That means the therapist decides at which exact time the resting or standing pressure is measured. However, values like the standing pressure show significant changes over time of assessment. Also, uneven pressure curves will not be smoothened, nor are there any automatic calculations of mean or average values to increase reproducibility. In contrary, algorithms allow appropriate detection e.g. for resting pressures or dynamic changes like pressure amplitudes.

Several methods to measure compression efficacy will be proposed in the following. Beside the measurement of efficacy of the compression device 112, such as the compression bandage, also other parameters like venous refilling time (section B) or safety of the bandage (section A and E) can be measured by the compression system 110 and, specifically, by the monitoring system 116.

Besides assessing of the compression system 110 and, specifically, the compression device 112, within predetermined time intervals, e.g. clinical visits or daily nursing service, efficacy can also be assessed continuously.

Several assessments can be done to judge efficacy or safety over the time of compression application. This continuous measurement can be done in the domestic environment or during normal activity of the user, also referred to as the patient. Further description is outlined under G-K.

A.) Measurement of the Resting Pressure $p_{rest}$

Figure 2:
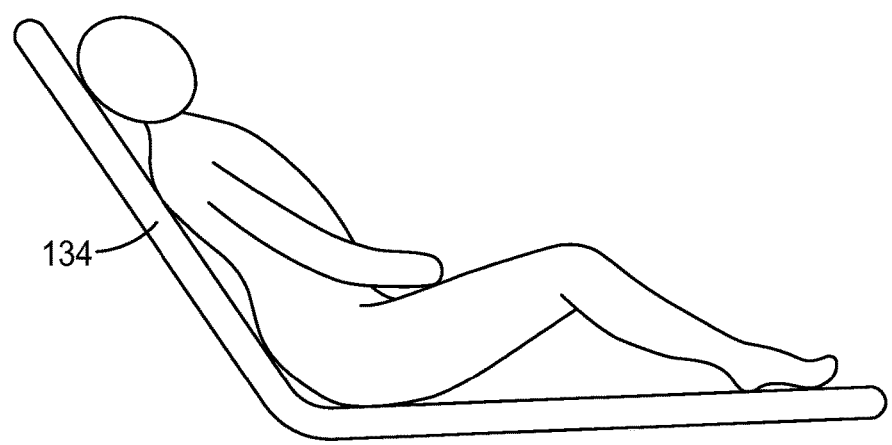
FIG. 2 shows a user in a resting position.

A first version of measuring the efficacy of the compression system 110, specifically of the compression device 112, is a measurement of the resting pressure $p_{rest}$. The resting pressure $p_{rest}$ describes the forces which are built up only by the compression system 110. The resting pressure specifically may be a supine pressure, i.e. a pressure taken with the patient in a supine position as depicted in FIG. 2. The resting pressure specifically may be reduced over time due to material fatigue, slippage of bandage or limb volume reduction.

For measurement of the resting pressure $p_{rest}$, the patient has to be in a relaxed position, such as in a sitting or a lying position, also referred to as a supine position, as shown in FIG. 2. Preferably, during the measurement of the resting pressure, the foot rests relaxed on a bed 134 or couch, wherein the knee of the patient preferably is slightly flexed and the calf preferably is completely free of the bed surface.

The measurement preferably may be activated by activating a pushbutton, keypad or touch screen, such as by using one or more of the user interfaces of the evaluation unit 126. In the following, pressure values are acquired by using the pressure sensor 118. The pressure values may be acquired over time intervals, such as time intervals of 1 second, with time interval, such as 10 measurements every 100 ms per time interval. The pressure values may be stored by the evaluation unit 126. As an example, averaged pressure values over the time intervals may be calculated and stored. Thus, an averaged value of the pressure values over the time interval may be calculated and stored, such as a geometric mean value, an arithmetic mean value or a median over the ten pressure values within each time interval of 1 s.

Optionally, the averaged pressure value, such as the median value, may be compared from one interval to the next time interval. If a pressure variation within 5 consecutive time intervals is below a specific threshold, such as below 0.1 to 10%, preferably below 2%, the resting pressure may be stored by the evaluation unit 126.

Thus, generally, in this embodiment or other embodiments of the present invention, the resting pressure $p_{rest}$ may be measured after a period of stabilization of a measurement curve of pressure values acquired using the pressure sensor 118, such as in case the variation of pressure values is below a predetermined threshold, such as a threshold of 0.1 to 10%, preferably below 2%. Therein, in this embodiment or other embodiments, the full measurement curve may be evaluated or an averaged measurement curve, such as a measurement curve containing pressure values averaged over a time interval and/or averaged over a number of measurement points.

To shorten the time required for the measurement and/or to avoid having to wait until a threshold value is reached, the median of the previous 5 time intervals can be calculated for example upon command (for example via push button) or automatically (for example if a certain, select measurement time (e.g. 2 minutes) has elapsed). The median is then stored as the sub-bandage resting pressure.

Generally, as outlined above, other time intervals may be used. Thus, in this embodiment or in other embodiments, instead of a time interval of 1 second, a shorter time interval, such as a time interval of 0.1 s, or a longer time interval, such as a time interval up to 60 s, may be defined.

Instead of 10 measurements within each time interval, also a different number of measurements within each time interval may be taken. Thus, a number of less than 10 measurements, such as 3 measurements, or a number of more than 10 measurements, such as up to 1000 single measurements, may be taken.

Figure 6:
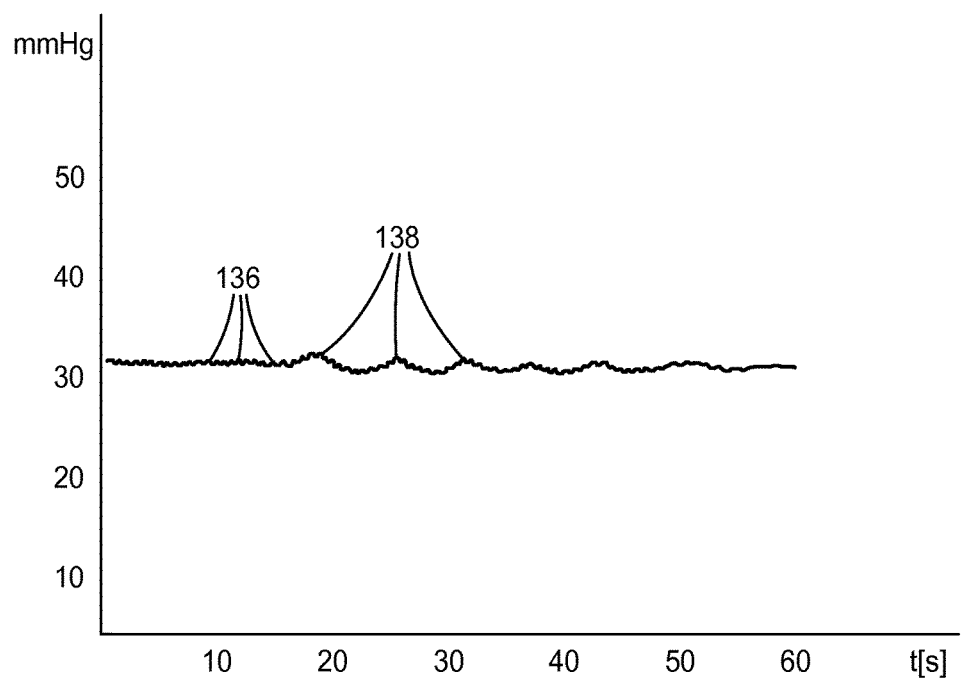
FIG. 6 shows a measurement curve including arterial pulsations of pressure values.

In FIG. 6, a typical measurement curve of pressure values taken over a normal period of time, without any major position changes, is shown. Therein, on the vertical axis, the pressure values are given, provided in mmHg, wherein the horizontal axis is the time axis t in seconds.

As can be seen, the measurement curve of pressure values typically shows physiological periodic alterations due to the arterial pulsation (reference number 136) and due to the respiratory activity (reference number 138). As outlined above, it is possible to detect these arterial pulsations and to detect the amplitude of these pulsations. It is even possible to evaluate the amplitude of these pulsations and to compare this amplitude to a threshold, in order to be able to generate a warning in case the amplitude of the arterial pulsations is too low. Further, in view of the above-mentioned averaging over a plurality of pressure values, the arterial pulsations generally show that for analysis of arterial pulsation a minimum number of single measurements for averaging is desirable at least six per second. It will be appreciated that the higher the number, the more accurate the arterial pulsation analysis.

The above-mentioned measurements mainly refer to a measurement of the resting pressure $p_{rest}$, specifically an initial measurement of the resting pressure as a baseline measurement. Further, as outlined above, at least one standing pressure $p_{standing}$ is measured, specifically at least one so-called extended standing pressure $p_{standing, extended}$.

For measuring the standing pressure, after the measurement in the supine position, the system generally may invite the user to perform the measurement of the standing pressure, such as by inviting the user to change position into the standing position. For this purpose, the evaluation unit 126 may give an acoustical or numerical signal. This signal may be also used to remind changing the position to standing.

Directly after application of the compression device 112, the resting pressure $p_{rest1}$ may be too low or too high because of a false application technique. In order to detect this false application technique, the resting pressure $p_{rest1}$ may be compared to one or more threshold values. As an example, if the resting pressure $p_{rest1}$, preferably the supine resting pressure, is below 50 mmHg, the monitoring system 116, specifically the evaluation unit 126, may indicate that the compression is ineffective and has to be changed. This threshold can also be lower as detailed below:

$P_{rest1}$<50 mmHg (preferably <20 mmHg, more preferably <15 mmHg, most preferably <10 mmHg)→change compression, pressure too low Also, as indicated above, $p_{rest1}$ may be too high. Typically, values higher than 60 mmHg are considered to be intolerable or may cause circulatory disorder:

$P_{rest1}$>60 mmHg (more preferably >80 mm Hg, most preferably >100 mmHg)→change compression, pressure too high Generally, the resting pressure, such as the resting pressure measured in a supine position, decreases over time due to material fatigue, slippage of bandage or limb volume reduction. This process may also be monitored by comparing one or more key figures to one or more threshold values. Thus, in case some time after application of the compression device 112 the resting pressure $p_{rest2}$ drops below a threshold such as below 40 mmHg, the evaluation unit 126 may indicate that the compression device 112, such as the compression bandage, is not effective any longer. This threshold can also be lower as indicated below:

$p_{rest2}$<40 mmHg (preferably <15 mmHg, more preferably <25 mmHg, most preferably <5 mmHg)→change compression The resting pressure could also increase over time e.g. due to changes (e.g. slippage) in the compression system such that $p_{rest2}$ could be too high (e.g. values higher than 60 mmHg):

$P_{rest2}$>60 mmHg (preferably 22 80 mmHg, most preferably >100 mmHg)→change compression, pressure too high As the resting pressure such as the supine pressure may show relevant inter-individual variations, a further option may be to calculate the absolute change or the relative change of the actual $p_{rest2}$ in comparison to the initial $p_{rest1}$. Thus, again, the absolute change of the relative change may be compared to one or more threshold values.

As an example, if $p_{rest2}$, in comparison with $p_{rest1}$, is reduced by more than 20% (more particularly more than 40%), such that the remaining resting pressure $p_{rest2}$ is lower than 80% (more particularly lower than 60%) as compared to the baseline resting pressure $p_{rest1}$, the evaluation unit 126 may indicate that compression is not effective any longer:

$$(P_{rest2}/p_{rest1}) \times 100\% < 80\%, \text{ preferably } <60\% \rightarrow \text{change compression}$$

As further indicated above, in this or other embodiments of the present invention, two or more key figures may be combined. As an example, absolute values of the resting pressure may be compared to one or more thresholds and, at the same time, a combination of two key figures may be compared to one or more thresholds. As an example, the evaluation unit 126 may be adapted to monitor that the actual resting pressure $p_{rest2}$ does not fall below 60% compared to initial $p_{rest1}$ and, further, does not fall below an absolute pressure threshold of 15 mmHg. All threshold values described above may be combined this way.

B.) Measurement of the Extended Standing Pressure $p_{standing, extended}$

As outlined above, the monitoring system 116 and the method according to the present invention use the so-called extended standing pressure $p_{standing, extended}$ as a key figure for assessment of efficacy of the compression device 112. The extended standing pressure is measured by using a modified process of measuring the pressure in the upright standing position. Standing position can mean that the patient is standing on both feet without any movements. In the best case, the patient would have both hands holding on something to avoid muscle contractions for balancing. A more realistic, alternative approach would be that the patient is standing in elevated position (e.g. a step) on the non-investigational leg. The leg with the pressure sensor should not be moved and should hang without contact to the floor.

Figure 3:
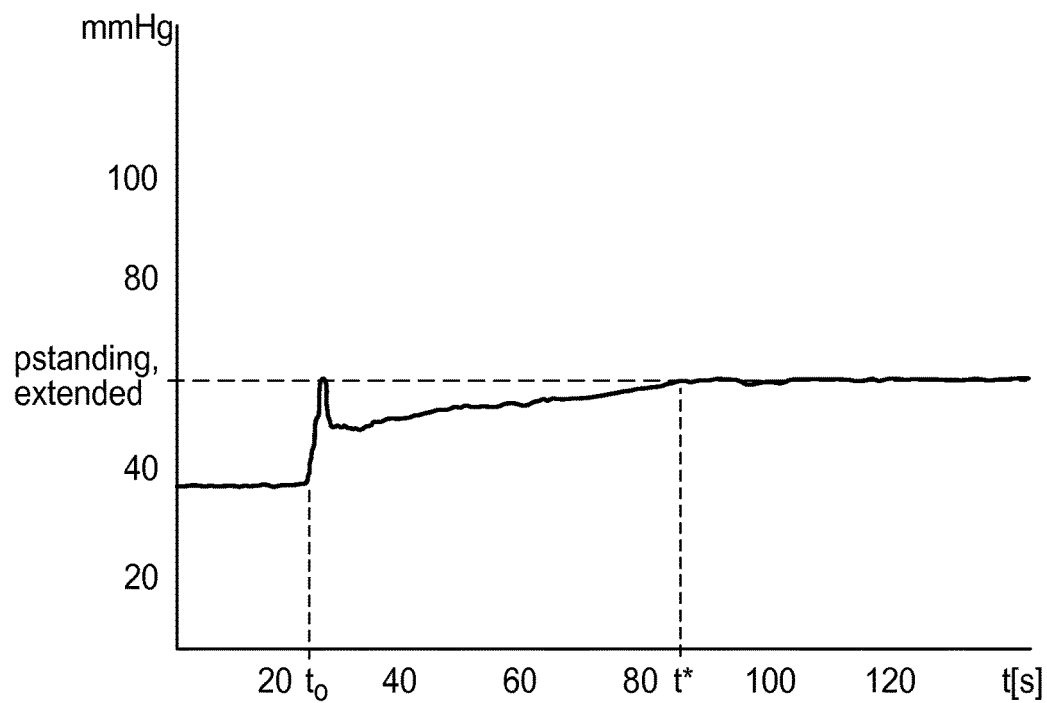
FIG. 3 shows a measurement curve of pressure values acquired after a position change into a standing position.

In FIG. 3, a measurement curve of pressure values of a healthy volunteer is depicted. Initially, before the position change, a resting pressure $p_{rest1}$ of approximately 35 mmHg is detected. After moving into the standing position, which takes place approximately at $t_0$, an overall increase in pressure compared to the resting pressure is observed. It will be appreciated that the move into the standing position typically causes a short, spike-like pressure peak(s) just after $t_0$ and any such pressure peak should be disregarded in determination of standing pressure. In FIG. 3, just after $t_0$ the pressure peaks and subsequently thus falls to a value of approximately 48 mmHg, and thereafter, the pressure then increases as a result of venous filling to a pressure level of approximately 56 mmHg as an asymptotic value. Venous filling takes some time (approximately 40-90 s). In case of chronic venous disease including venous valve insufficiency, short refilling times will occur. The period of refilling time may also be used as a general criterion as will be described later.

As outlined above, if a compression device 112 becomes too loose because of material fatigue, volume reduction of the included leg, slippage of the system, or a combination, the system loses some of its capacity to keep the venous filling forces inside the compressed area. In other words, the system is less effective.

As can be seen in FIG. 3, the pressure asymptotically approaches an asymptotic endpoint value due to venous filling. In conventional measurements of the standing pressure $p_{standing}$, the medical staff will simply measure the standing pressure at a predetermined point in time after the position change or at a point in time at which the measurement curve appears to have reached its endpoint value. This procedure, however, implies a specific irreproducible and subjective component. Therefore, according to the present invention, the extended standing pressure $p_{standing, extended}$ is determined. The extended standing pressure is typically measured in a stable upright position of the patient. After activation of the monitoring system 116, e.g. by pushbutton activation, the monitoring system may start to continuously acquire pressure values. Therein, optionally, as outlined above, averaging may take place, such as an averaging within time intervals of 1 second including 10 single measurements each. The average or preferably median of these 10 pressure values for each 1 second interval may be calculated continuously.

Figure 4:
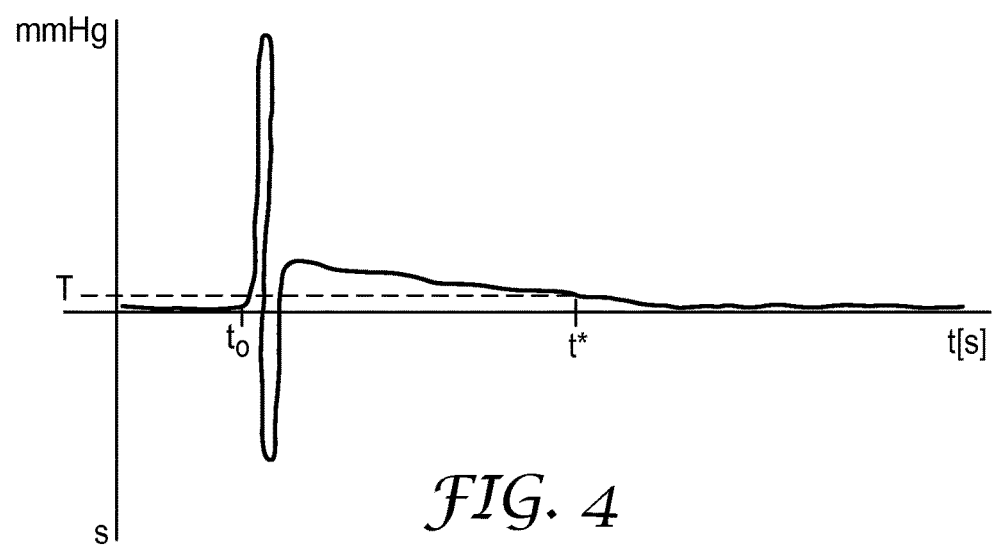
FIG. 4 shows a slope of the measurement curve of FIG. 3.

The evaluation unit 126 automatically evaluates the slope of the measurement curve and compares the slope to a predetermined threshold. In FIG. 4, the slope of the measurement curve of FIG. 3 is depicted. This slope simply may be the first derivative of the measurement curve of FIG. 3. Therein, the vertical axis may denote the slope in arbitrary units, such as in mmHg per time. As soon as the slope in FIG. 4 reaches a predetermined endpoint threshold value, denoted by T in FIG. 4, the evaluation unit 126 may automatically recognize that an endpoint of change in the measurement curve has been reached. In FIG. 4, this endpoint on the horizontal axis is denoted by t*. The pressure value in FIG. 3, which is acquired at t* or after t*, is assigned to the extended standing pressure $p_{standing, extended}$.

As an example, in this embodiment or other embodiments, the endpoint threshold value T may be equal to or less than 0.5 mmHg per second, preferably equal or less than 0.05 mmHg per second, most preferably equal or less than 0.01 mmHg per second.

In the exemplary embodiment depicted in FIG. 3, the median pressure differences of each 1 second time interval diminish when the measurement curve asymptotically levels out. If 5 consecutive time intervals show a pressure increase of less than 0.05 mmHg per second (which amounts to less than 0.25 mmHg per 5 time intervals) the system will store the standing pressure as the extended standing pressure $p_{standing, extended}$. As outlined under A, the median of the previous 5 time interval pressures may be stored as the extended standing pressure. All variations of criteria (e.g. length of time interval, number of single measurements) described under A are applicable for the measurement of the standing pressure also.

Also, the user could manually activate the monitoring system 116 by e.g. pushbutton to directly start measurement and documentation of the standing pressure. After completing measurement in the standing position, the system may provide an acoustical or optical signal. This signal may be also used to remind changing the position to walking as outlined later.

In this embodiment or any other embodiments, the extended standing pressure may be used instead of the standing pressure as determined in a conventional way, such as for any subsequent evaluation of the efficacy of the compression system 110 of the compression device 112. The standing pressure as determined in a conventional way may, however, be used in addition, such as as an additional key figure.

Directly after application of the compression system 110, the standing pressure $p_{standing1}$ or the extended standing pressure $p_{standing, extended1}$ are usually higher than in every subsequent measurement ($p_{standing2}$, $p_{standing, extended2}$) performed at a later point in time. Initially $p_{standing1}$ and/or $p_{standing, extended1}$ should be higher than a predetermined threshold, such as 40 mmHg. Generally when using $p_{standing1}$ and/or $p_{standing, extended1}$ as a key figure, a threshold of 40 mmHg or lower may be used:

$p_{standing1}$ and/or $p_{standing, extended1}$<40 mmHg (preferably <30 mmHg, most preferably <20 mmHg)→change compression.

The measurement of the extended standing pressure and, optionally and additionally, the conventional standing pressure, may be repeated at a later point in time, such as after several minutes, several hours or even several days. As indicated above, the values derived thereby may be used as additional key figures and will be denoted as $p_{standing2}$ and $p_{standing, extended2}$ in the following. Again, these key figures may be compared to one or more threshold values.

Thus, as an example, the standing pressure $p_{standing2}$ and/or the extended standing pressure $p_{standing, extended2}$ should not fall below a threshold of 35 mmHg or lower:

$p_{standing2}$ and/or $p_{standing, extended2}$<35 mmHg (preferably <25 mmHg, most preferably <15 mmHg)→change compression Both the extended standing pressure and the conventional standing pressure may be used for deriving further key figures for evaluating the efficacy of the compression device 112. Thus, as both the standing pressure and the extended standing pressure typically show inter-individual differences, a further option is to document the relative change of the actual $p_{standing2}$ and/or $p_{standing, extended2}$ in comparison to the initial (extended) standing pressure $p_{standing1}$ or $p_{standing, extended1}$, respectively, performed directly after application of the compression device 112. If $p_{standing2}$ and/or $p_{standing, extended2}$, respectively, is reduced by more than 20% (in particular more than 40%), so that it is lower than 80% (in particular lower than 60%) compared to baseline $p_{standing1}$ or $p_{standing, extended1}$, respectively, the evaluation unit 126 may indicate that the compression is not effective any longer.

Generally, in the present example or in other embodiments of the present invention, the threshold value for $p_{standing2}$ and/or $p_{standing, extended2}$ indicating inefficacy can be 80% or preferably 60%:

($p_{standing2}/p_{standing1}$)×100% and/or ($p_{standing, extended2}/p_{standing, extended1}$)×100%<80%, preferably <60%→change compression device Also both, absolute and relative thresholds can be combined, e.g. the actual $p_{standing(, extended)2}$ must not fall below 35 mmHg and the percent ratio of actual $p_{standing(, extended)2}$ to the previous $p_{standing(,extended)1}$ must not fall below 60%.

All threshold values described above can be combined this way.

The time period needed between changing from the resting position, such as the supine position, to the standing position of the patient until the time when the pressure does not further increase may also be used as a diagnostic criterion of chronic venous disease. Thus, in the example depicted in FIGS. 3 and 4 as well as in other examples, the time span from the position change ($t_0$) to the endpoint ($t^*$) may be used as a further key figure, indicating a refilling time $t_{refill}=t^*-t_0$. Especially functional changes due to valve insufficiency and venous ectasia (dilatation) may be judged by this time interval. Venous refilling also may change from baseline to follow up measurements. Also different compression systems might have varying refilling times.

The more compression a system delivers to the extremity, the more these forces counteract venous dilatation and consecutively valve insufficiency. This positive effect to the venous system can lead to longer refilling time. The refilling time could hence also be used to assess how effective the compression system influences venous reflux.

In this example or in other examples of the present invention, when using the refilling time as a key figure, the refilling time ($t_{refill}$) may be measured more than once, at different points in time. Thus, as an example, the refilling time may be measured at baseline and at follow-up. Differences between baseline and follow-up, again, may be compared to one or more threshold values. Thus, as an example, the difference of less than 5 seconds between refilling times measured at different points in time may be considered optimal, while differences in refilling times of greater than five seconds, more particularly greater than 10 seconds may be considered as an indication to change the compression system.

$t_{refill1}-t_{refill2}$>5 s (preferably >10 s)→change compression

Furthermore, a refilling time which may be overall too short may indicate a venous valve insufficiency and could be an indication for a warning for the user to consult with the medical practitioner. Thus, as an example, as an upper threshold value for the absolute refilling time may be 30 seconds:

$t_{refill}$<30 s→warning signal (short refilling time/consult medical practitioner)

Figure 7:
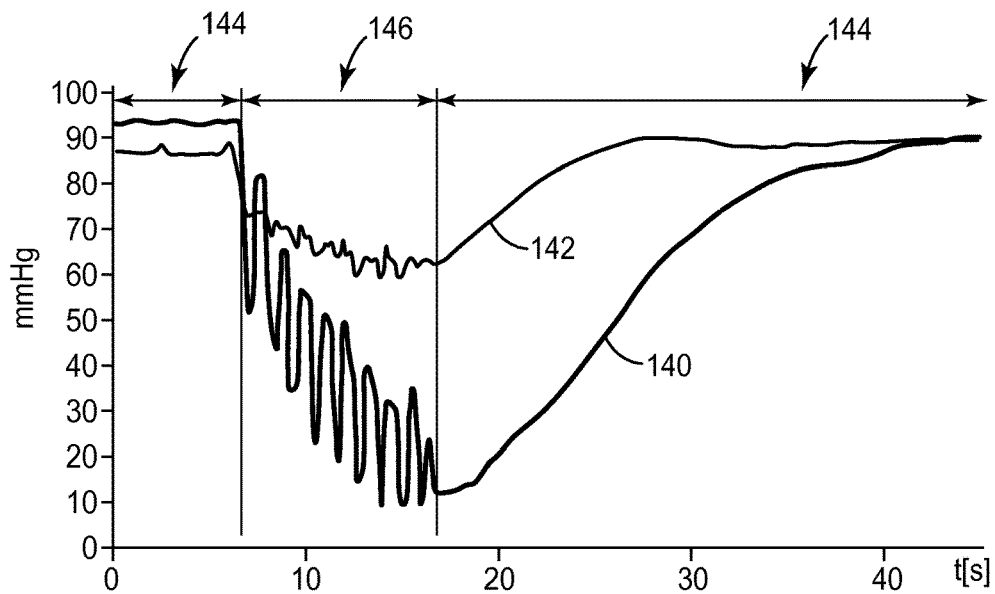
FIG. 7 shows measurement curves including refilling curves of normal limbs and limbs with incompetent venous valves.

In FIG. 7, measurement curves 140 and 142 are depicted, wherein measurement curve 140 shows a measurement curve of a normal limb, whereas measurement curve 142 shows a measurement curve of a limb with incompetent venous valves. Therein, time spans 144 denote periods in which the person is standing, whereas time span 146 denotes a period in which the person is walking. As can be seen, the refilling time for the limb with incompetent venous valves, the refilling time is significantly shorter than for the limb with normal venous valves.

Beside the venous refilling time, also the shape of the measurement curves, such as the measurement curves 140 and 142 in FIG. 7 or the measurement curve in FIG. 3, can act as a key figure and may provide information about the anatomical fit of the compression device 112 and its stiffness. With good anatomic fit, the increase of pressure typically is moderate directly after position change to standing. In this phase, the initial increase of volume does not find very strong counter bearing due to the compression system. With further volume gain, the tensile elastic limit is advanced and hence the pressure curve becomes steeper until the increase alleviates and the curve approximates to the asymptote. A slightly sigmoidal shape of the curve is typical for a good anatomic fit and sufficient stiffness of the compression device 112.

C.) Measurement of Static Stiffness

Further, a significant key figure for evaluating the efficacy of the compression device 112 may be the so-called static stiffness index SSI. Again, the static stiffness index, which is generally known in the art, may be calculated by using the conventional standing pressure and/or by using the extended standing pressure, as discussed above. In case the conventional standing pressure is used, the expression "SSI" will be used in the following, whereas, in case the extended standing pressure is used, the expression "ESSI" (extended static stiffness index) will be used in the following.

The static stiffness index generally denotes the difference between the pressure in the resting position, such as in the supine position, and the pressure in the upright position. For effective compression of chronic venous insufficiency and leg ulcer, high stiffness is considered to be most effective. After some days of application of the compression device 112, such as after some days after application of a compression bandage, the SSI (or ESSI, respectively) may have changed in comparison to the baseline status directly after application of the compression device 112. This effect may be caused by material fatigue, slippage of the bandage or the therapeutic effect of limb volume reduction.

For assessing the SSI or ESSI, respectively, the sub-bandage pressure may be measured in the resting position first, by measuring as explained above in section A. For assessing the standing pressure $p_{standing}$ or the extended standing pressure $p_{standing, extended}$, reference may be made to section B above.

After the monitoring system 116 has finished measuring the resting pressure, an acoustical signal may be given. Additionally or alternatively, other invitations for changing position may be provided to the user. After this signal, the patient should change to the standing position. As indicated above, after some time, the pressure signal becomes stable and the evaluation unit 126 may automatically detect the extended standing pressure as described in section B above. Additionally or alternatively, as explained above, a conventional method may be used for measuring the standing pressure.

Instead of using actual measurements for determining the static stiffness index and/or the extended static stiffness index, additionally or alternatively, values provided by data input may be used. Thus, another procedure may be to enter the information of the patient's position via a pushbutton, keypad or touch screen. After the system gets this information of position change, the system continues to measure pressure in time intervals for evaluation of the standing pressure as described in section B above.

Generally, the evaluation unit 126 may document two pressures, one in resting position, one in standing position.

The static stiffness index (SSI) may be defined by the following formula:

$$SSI = p_{standing} \text{ [mmHg]} - p_{rest} \text{ [mmHg]}$$

Similarly, the extended static stiffness index (ESSI) may be defined by:

$$ESSI = p_{standing, extended} \text{ [mmHg]} - p_{rest} \text{ [mmHg]}$$

Figure 8:
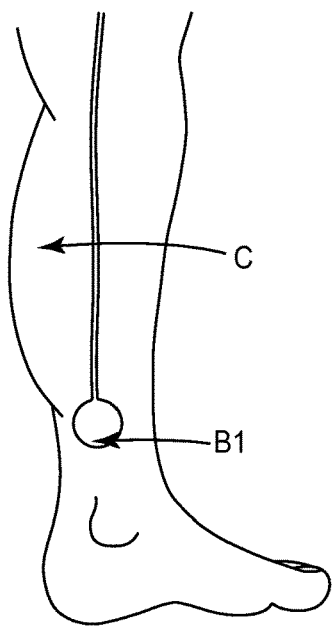
FIG. 8 shows different positions where a pressure sensor may be positioned on the lower leg of a human.

Several parameters may have an influence on the SSI or ESSI, respectively. Thus, SSI and/or ESSI may be related to a bandage material, the degree of bandage stretch when applied by the therapist, a size and an activity of the muscles such as the calf musculature or the mobility of certain joints, such as the mobility in ankle joints, especially in elderly patients and it may be related to the location on the limb, where the pressure is measured. (see FIG. 8). Over time of bandage application, the SSI or ESSI, respectively, may change indicating that the compression device 112, such as the compression bandage, is not effective any more.

In the above-mentioned publication by Mosti et al., some experimental results are disclosed, which compare measurements taken immediately after the application of the compression device 112 and measurements taken one week after application, for a plurality of 100 patients. The data reveal that effective ulcer healing correlates with a SSI that does not drop significantly over time. By using the extended static stiffness index ESSI instead of the conventional SSI, as proposed herein, the reproducibility and precision of the key figure SSI/ESSI may further be increased.

Again, in this example or in other exemplary embodiments of the present invention, the key figure of the static stiffness index and/or the key figure of the extended static stiffness index again may be compared to one or more threshold values. Thus, generally, as for all other key figures, the evaluation unit 126 may be adapted to perform this comparison automatically. Again, the key figures may be determined repeatedly at different points in time, such as immediately after application of the compression device 112 as well as after a certain time span after application of the compression device 112, such as after several minutes, several hours or even several days. As an example, a lower threshold for the initial static stiffness index and/or for the initial extended static stiffness index may be selected. Thus, as an example, directly after application of the compression device 112 such as the compression bandage, the initial SSI ($SSI_1$) and/or the initial ESSI ($ESSI_1$) may be assessed by the monitoring system 116, such as by the evaluation unit 126. The evaluation unit 126 may be programmed to indicate inefficacy of the compression device 112, if the $SSI_1$ and/or the $ESSI_1$ is lower than a select threshold of e.g. 10 mmHg or 15 mmHg, respectively (or preferably an even lower threshold of 5 mmHg or 10 mmHg, respectively):

$$SSI_1 = p_{standing1} \text{ [mmHg]} - p_{rest1} \text{ [mmHg]}$$

$$SSI_1 < 10 \text{ mmHg (preferably} < 5 \text{ mmHg)} \rightarrow \text{change compression}$$

And/or:

$$ESSI_1 = p_{standing, extended1} \text{ [mmHg]} - p_{rest1} \text{ [mmHg]}$$

$$ESSI_1 < 15 \text{ mmHg (preferably} < 10 \text{ mmHg)} \rightarrow \text{change compression}$$

As indicated above and as valid for any key figure K used for assessment of the efficacy of the compression device 112, the key figure of the static stiffness index and/or the key figure of the extended static stiffness index may be determined repeatedly, such as by determining this key figure at a later point in time. Thus, for control of effective compression, a subsequent measurement of the SSI and/or ESSI may be performed at a later in time point.

Again, as valid for any type of key figure, the key figure determined at a later point in time again may be compared to one or more threshold values which may be different from the threshold values applied to the previously determined key figures. Additionally or alternatively, the key figure determined at a later point in time may be compared to the respective key figure previously determined.

Thus, as an example, the monitoring system 116 and, specifically, the evaluation unit 126, may indicate in efficacy in case the $SSI_2$ and/or the $ESSI_2$ are below a predetermined threshold value. Generally, in this embodiment or other embodiments, this threshold value may be lower than those described for $SSI_1$ and $ESSI_1$. As an example, the following comparisons may be performed by the evaluation unit 126:

$$SSI_2 = p_{standing2} \text{ [mmHg]} - p_{rest2} \text{ [mmHg]}$$

$$SSI_2 < 5 \text{ mmHg (preferably} < 3 \text{ mmHg)} \rightarrow \text{change compression}$$

And/or:

$$ESSI_2 = p_{standing, extended2} \text{ [mmHg]} - p_{rest2} \text{ [mmHg]}$$

$$ESSI_2 < 10 \text{ mmHg (preferably} < 4 \text{ mmHg)} \rightarrow \text{change compression}$$

Again, as the SSI and/or EESI typically show inter-individual variations, a further option may be to add the relative change of the actual $SSI_2$ and/or $ESSI_2$ in comparison to the initial $SSI_1$ or $ESSI_1$, respectively, the latter acquired directly after application of the compression device 112, such as directly after bandage application. If the actual $SSI_2$ and/or $ESSI_2$ is reduced by more than a predetermined threshold, such as 20%, preferably 40%, as compared to the initial value $SSI_1$ or $ESSI_1$, respectively, the monitoring system 116 and, specifically, the evaluation unit 126 may indicate that the compression device 112 is not effective any longer.

As an example:

$$SSI_2 = p_{standing2} \text{ [mmHg]} - p_{rest2} \text{ [mmHg]}$$

$$SSI_1 = p_{standing1} \text{ [mmHg]} - p_{rest1} \text{ [mmHg]}$$

$(SSI_2/SSI_1) \times 100\% < 80\%$, preferably $<60\% \rightarrow$ change compression And/or:

$$ESSI_2 = p_{standing,\ extended2} \text{ [mmHg]} - p_{rest2} \text{ [mmHg]}$$

$$ESSI_1 = p_{standing,\ extended1} \text{ [mmHg]} - p_{rest1} \text{ [mmHg]}$$

$(ESSI_2 : ESSI_1) \times 100\% < 80\%$, preferably $<60\% \rightarrow$ change compression Again, as for all the key figures, absolute and relative thresholds may be used and/or may be combined. Thus, as an example, the actual $SSI_2$ and/or $ESSI_2$ may be monitored in order not to fall below 60% compared to initial $SSI_1$ or $ESSI_1$, respectively, and also may be monitored in order not to fall below an absolute value of 5 mmHg or 10 mmHg, respectively. All threshold values described above may be combined this way.

D.) Measurement of Amplitudes

As outlined above, one or more amplitudes of measurement curves during a defined activity or movement of the user may be used as one or more additional key figures for determining the efficacy of the compression device 112.

Thus, as an example, due to calf muscle contraction within a rigid sleeve, mainly by the musculus gastrocnemius and soleus, the sub-bandage pressure typically shows short termed pressure peaks. These amplitudes, generally defined by the differences between the pressure values in the upper and lower pressure peaks in the measurement curve, may be used as another key figure and, thus, as another option for evaluating the efficacy of a compression device 112. Again, this key figure may provide an indication of how well an applied compression system 110 manages to keep forces produced by the muscle activity inside the compressed area.

Figure 5:
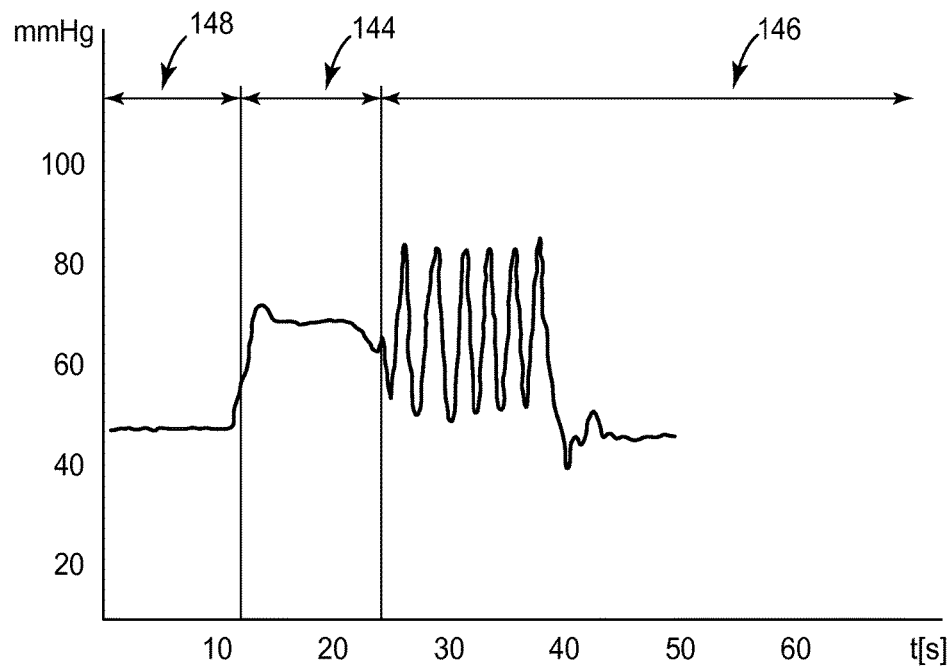
FIG. 5 shows a measurement curve of pressure values acquired during an activity of a user.

In FIG. 5, an example of a measurement curve acquired during a controlled movement of the user is depicted. In this figure, a period of resting (such as in the supine position) is denoted by reference number 148, whereas, as in FIG. 7, periods of standing and periods of walking are denoted by reference numbers 144 and 146, respectively. In this measurement as depicted in FIG. 5, the pressure sensor 118 was placed in a position denoted by B1 in FIG. 8, which shows a lower leg of the user. Instead of walking, any other type of controlled functional activity and/or exercise may be used.

As an example, for performing the measurement, the patient has to be in the upright position and has to walk on a belt or has to do other "defined" physical activities. Due to calf muscle contraction, the sub-bandage pressure shortly increases and immediately decreases again within the diastolic phase of muscle relaxation.

The monitoring system 116, specifically the evaluation unit 126, may automatically detect specific activities. Thus, the evaluation unit 106 may automatically detect that the patient is walking on a belt or stepper. See portion of the curve with its alternating pressure curve marked with the reference number 146 in FIG. 5. Thus, within the phasic curve as shown in FIG. 5, the evaluation unit 126 may detect Amplitude as key figure.

When monitoring amplitudes, the amplitudes may be evaluated statistically. A median or mean value may be formed and compared to one or more threshold values. Thus, as an example, if a median or mean amplitude is below a predetermined threshold of e.g. 40 mmHg, more particularly of 15 mmHg, the system may indicate that compression is not effective any more:

$Amplitude_{median}$ or $Amplitude_{mean} < 40$ mmHg, preferably $<15$ mmHg $\rightarrow$ change compression Median or mean amplitudes measured at different points in time may be compared. Thus, again, a ratio of these amplitudes may be formed and may be compared to one or more threshold values. As an example, the monitoring system 116 may indicate an efficacy of the compression device 112 in case $Amplitude_{median2\ or\ mean2}$ is less than 80% (preferably less than 60%), as compared to $Amplitude_{median1\ or\ mean1}$:

$(Amplitude_{median2}/Amplitude_{median1}) \times 100\%$ or $(Amplitude_{mean2}/Amplitude_{mean1}) \times 100\% < 80\%$, preferably $60\%$: $\rightarrow$ change compression Also both, absolute and relative thresholds may be combined, e.g. the actual median amplitude must not fall below 60% compared to the initial amplitude and also must not fall below 15 mmHg. All threshold values described above may be combined this way.

E.) Multiparameter Measurement of Pressure Values

A further method to assess efficacy of a compression system is to combine two or more key figures, such as two or more of the key figures listed above in sections A-D. Thus, the determination of each key figure, such as the key figures of sections A-D above, may be used as a single module for measurement. Additionally or alternatively, an arbitrary combination of key figures may be possible, which may lead to a multi-parameter assessment. A multi-parameter assessment may allow for a more precise and more reproducible assessment of a sub-bandage pressure profile.

Figure 9:
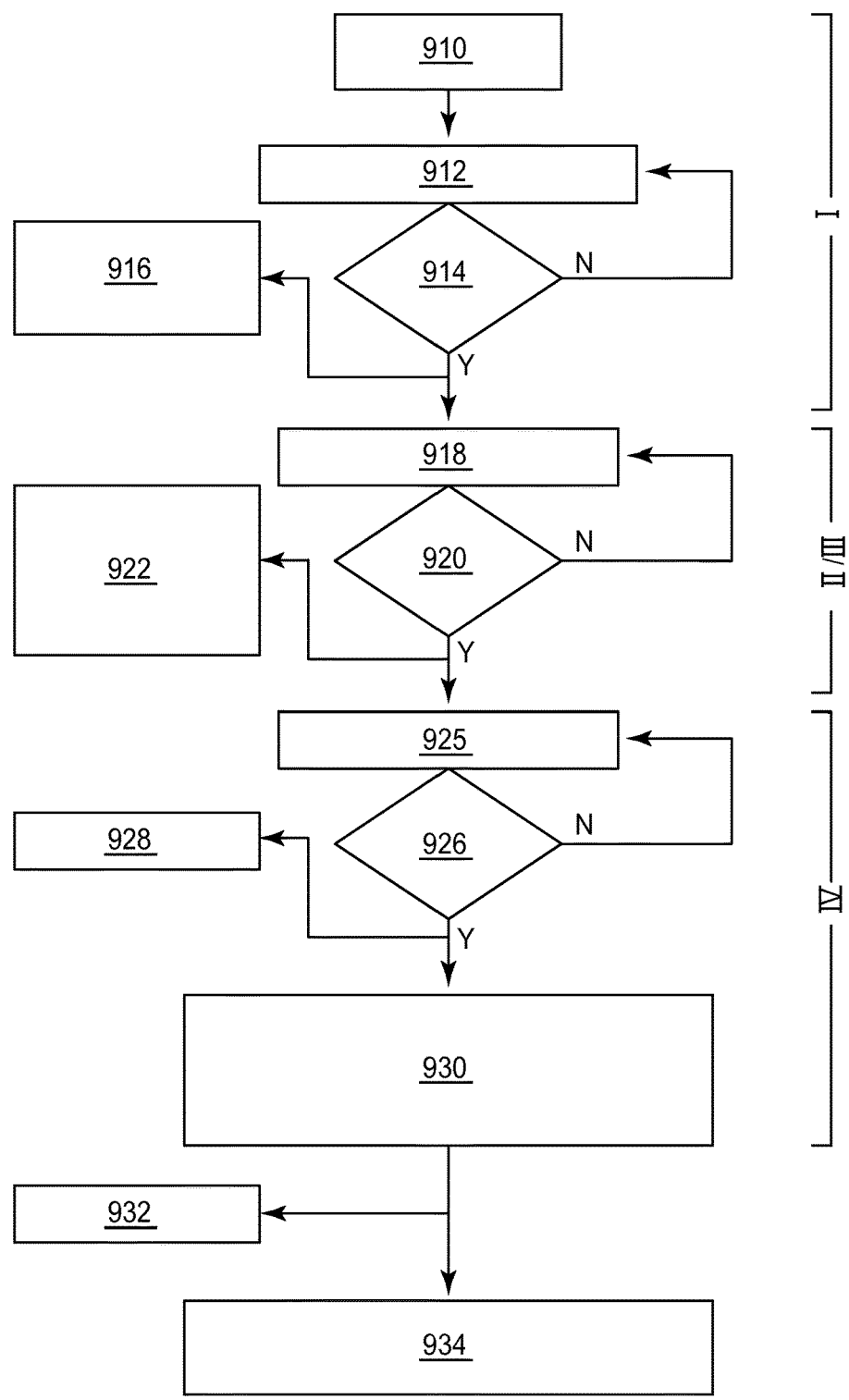
FIG. 9 shows a flow chart of an embodiment of a method for determining the efficacy of a compression device.

An example of a method using a multi-parameter assessment is depicted in FIG. 9. Therein, several (in this case four) consecutive measurement modules are used:

Module I: According to section A above, the resting pressure is measured.

Module II: According to section B above, the standing pressure $p_{standing}$ and/or the extended standing pressure $p_{standing,\ extended}$ is measured.

Module III: According to section C above, the SSI and/or ESSI is measured based on the resting and the standing pressure or on the resting and the extended standing pressure, respectively.

Module IV: According to section D above, the working pressure amplitudes are measured.

It shall be noted that any other combination of key figures is possible. Thus, an arbitrary combination of the modules I to IV above may be used.

In FIG. 9, the following method steps may be used:

910 Start by push button
912 Measurement of resting pressure
914 Query: Stable resting pressure? (Y: Yes, N: No)

916 Display result: $p_{rest}$ and display: "change position to standing position"
918 Measurement of standing pressure $p_{standing}$ and/or measurement of extended standing pressure $p_{standing,\ extended}$
920 Query: Stable standing pressure? (Y: Yes, N: No)
922 Display result: $p_{standing}$ and/or $p_{standing,\ extended}$, calculate and display SSI and/or ESSI, display: "change to walking"
924 Measurement of amplitude
926 Query: Stable amplitude? (Y: Yes, N: No)
928 Determine amplitude and optionally display result
930 Calculation of status (Baseline/Baseline versus Follow-up)
  Calculation of key figures (e.g. SSI, ESSI, etc.)
  Analysis of key figures (modules I-IV)
932 Display of results, e.g. status, key results, whether compression device should be changed (the latter could be done in the form of a traffic light, e.g. red light change compression device, green status is good and yellow warning) or other pertinent information
934 Store results, e.g. key values, status information, figures, etc. values, figure, key values For details of these steps, reference may be made to the disclosure of the single modules above. Although not specifically depicted in FIG. 9, in case a multiple (e.g. two or more) NO answers to any one of the queries under 914, 920, 926 occurs, to avoid a continuous looping at that point, the method can be arranged such that after a certain select number of NO answers (e.g. two or three) a routing is provided directly down to 932 so that the issue (e.g. unstable resting pressure measurement) can be displayed.

Interface Between Algorithm and the Evaluation Unit 126 and/or Pressure Sensor 118

In this embodiment or in other embodiments of the present invention, the pressure sensor 118 or, in case a plurality of pressure sensors 118 is used, each of the pressure sensors 118 may comprise an electronic identifier, such as a contactless electronic identifier, which allows for a unique identification of the pressure values provided by the respective pressure sensor 118. As an example, a RFID may be used as an electronic identifier.

The electronic identifier, such as the RFID, within the pressure 118 sensor may be activated by first readout of the reader. Thus, the evaluation unit 126 may comprise a reader for reading out the electronic identifier.

The monitoring system 116 may further be adapted to automatically detect new components, such as newly implemented pressure sensors 118. If the monitoring system 116 detects a new electronic identifier, such as a new RFID, the monitoring system 116 may save all measured values as the baseline status. Subsequent measurements which may be repeated within a predetermined time span, such as within 3 hours after first activation, may overwrite the first baseline values. This procedure may allow for repeating false baseline measurements. The predetermined time span, such as the period of 3 h, may as well be chosen shorter or longer than 3 h, such as 10 minutes or up to 24 h.

After a waiting time according to the predetermined time span, such as after a period of 3 h, any following measurements may be stored as follow-up assessments for the compression system 110. By using the electronic identifier, such as by using the RFID, the monitoring system 116, specifically the reader, may automatically assign the follow-up values to the right patient and all subsequent values will be compared to the appropriate baseline values. Due to this procedure, deletion of data by mistake may be excluded.

Further, a mixing up of patient data may be avoided by using electronic identifiers. Thus, a re-use of the sensor electronics may be avoided in order to avoid false RFID assignment to another patient, which may lead to incorrect calculation of baseline versus follow-up data.

In the method depicted in FIG. 9, various options exist for combining the phases and/or for evaluating the phases. Several options will be given in the following:

Option 1:

Each phase can be assessed separately. So, the resting pressure, standing pressure, extended standing pressure, the SSI, the ESSI and the amplitude may each be used as a single measurement. A button may be used to get into the right mode of compression measurement (e.g. resting pressure).

Option 2:

Combinations including a fixed sequence of measurements as shown in the flow-chart may be used to receive a more comprehensive picture of the actual properties of the compression device 112.

For this purpose, a start button may be activated to start the measurement. The resting pressure may be assessed and documented automatically as described in section A above. An acoustical and/or numerical signal may provide information that the monitoring system 116 has completed the first measurement in resting position. If the measurement should be repeated immediately (e.g. due to false position of the patient), a ("start") button may be pushed again.

An acoustic signal may invite the user or patient to change into the standing position. As described in section B above, the device may automatically detect the accurate standing pressure. An acoustical and/or numerical signal may provide information that the monitoring system 116 has completed the second measurement in the standing position. If the measurement should be repeated immediately (e.g. because the patient has been moving excessively), a "start" button may be pushed again.

On the basis of the resting pressure and the standing pressure or the resting pressure and the extended standing pressure, the monitoring system 116 may automatically calculate the third parameter SSI and/or ESSI, respectively, as disclosed above in section C.

After an appropriate invitation by the monitoring system 116, such as after an acoustic signal, the patient may start to walk on a treadmill, stepper or another device that allows continuous and periodic exercise, preferably in a controlled and reproducible way. As described in section D above, the monitoring system 116 may automatically measure the working pressure amplitude. An acoustical and/or numerical signal may provide information that the monitoring system 116 has completed the measurement in the walking position. If the measurement should be repeated immediately (e.g. because the patient did not walk regularly), a "start" button may be pushed.

Finally, the monitoring system 116 may either display all values numerically, including the resting pressure, the standing pressure, the extended standing pressure, the SSI, the ESSI, the amplitude, or any arbitrary combination thereof, as well as, optionally, appropriate changes with reference to the respective baselines, such as the percentage changes compared to baseline. Additionally or alternatively, the monitoring system 116 may automatically calculate if the compression device 112 is still effective, such as by evaluating one or more key figures, e.g. according to one or more of the algorithms and/or threshold values disclosed in sections A-D above. If these calculations are based on more than one value, the thresholds given under A-D might change within the given ranges.

Generally, in this embodiment or other embodiments, an information regarding the efficacy of the compression device 112 (such as whether the compression device 112 is still effective or not) may be provided to the user in an arbitrary way, such as by visual display. As an example, a "traffic light" type display may be used, indicating an efficacy by a green light, an intermediate or reduced efficacy by a yellow light, and an inefficacy by a red light.

F.) Measurement of Arterial Pulsations

As outlined above, specifically with respect to FIG. 6, one or more key figures derived from the detection of arterial pulsations may be used for determining the efficacy of the compression device 112. Thus, generally, sufficient arterial perfusion is a prerequisite for adequate tissue metabolism and healing processes in patients with chronic leg ulcer. Compression with too high resting pressure may cause arterial under-perfusion and may cause delayed or interrupted wound healing. According to Pascal's law, pressure typically is equally distributed in tissues. This generally means that volume changes synchronous to arterial pulsation can be measured under a stiff compression device 112. In case the pulsation is recognized by the monitoring system 116, arterial macro-perfusion is likely to be existent under the compression device 112. This information can be valuable for safety reasons especially in patients with arterial perfusion disorders.

Thus, in addition or alternatively to some of the key figures disclosed in sections A-E above, one or more key figures derived from arterial pulsations may be used. Thus, periodic oscillations in one or more of the measurement curves may be detected, preferably over the whole period of measurement time. Periodic oscillations due to arterial pulsations (denoted by reference number 136 in FIG. 6) typically are to be expected within a frequency band of 0.7 to 1.8 Hz. The frequency band can also be wider with 0.5 up to 2.5 Hz. As outlined above, electronic filters and/or mathematical evaluation means may be used for detecting the arterial pulsations within the measurement curves, such as Fourier analysis. Thereby, the frequencies of pulse, breathing (respiratory activity 138 in FIG. 6) and other periodic loads (e.g. Walking, see section D above) may be determined and may be distinguished from arterial pulsations.

G.) Assessment of Patient Activity Profile

During position changes of the leg, walking or training exercise, sub-bandage pressure typically changes and venous blood is consecutively shifted in proximal direction back to the central circulation. Typically, one important aspect of sufficient and appropriate compression therapy is the cooperation of the patient. Physical exercise, walking, biking or in minimum some movement, increases the venous flow under compression therapy.

Generally, by using the monitoring system 116 having the at least one pressure sensor 118, an activity profile of the patient may be recorded and may be evaluated. Thus, two or more intensity levels may be identified in one or more continuous measurement curves of pressure values provided by the pressure sensor 118, wherein, for example, for each intensity level of the activity profile, the monitoring system 116 may evaluate how much time the patient has spanned within the respective intensity level.

Generally, an algorithm may be used which is capable of finding predefined pressure alterations which are typically observed under movement. The algorithm may be capable of detecting pressure alterations, here defined as Exercise Events (EE). An EE is defined as an absolute (positive or negative) change of pressure larger than 1-30 mmHg, preferably 5 mmHg. This pressure alteration should occur within a time period of 0.1-10 s, preferably 1 s. EEs may be recorded over the whole time of application of the compression device.

Over one hour or up to one or more days, the amount of EEs per time period (e.g. 1 hour) may be calculated and rated on an activity index, such as on a 1-10 Activity Index (AI) scale. A low AI means no or low activity, a higher Index means that the patient sufficiently moved and consecutively supported the clinical benefit of the compression system. The scale for AIs can be larger with up to 1-100 for more precise differentiation of activity intensities.

Further, EEs with varying intensities may be distinguished, e.g. $EE_1$ with $\geq$3-6 mmHg, $EE_2$>6-10, $EE_3$ with >10 mmHg absolute pressure difference:

$$EE_1 \geq |3\text{-}6 \text{ mmHg}|$$

$$EE_2 > |6\text{-}10 \text{ mmHg}|$$

$$EE_3 > |10 \text{ mmHg}|$$

EEs with different intensities may also be weighted, so that one $EE_3$ has more impact than one $EE_1$ for example:

$$\text{Impact EE1} < \text{Impact EE2} < \text{Impact EE3}$$

Instead of 3 intensity levels, a different number of intensity levels may be used. Thus, also 2-100 EEs can be defined for more precise activity evaluation.

Further, other key figures may be used in addition. Thus, one or more of the key figures $SSI_1$, $SSI_2$, $ESSI_1$, $ESSI_2$ and amplitudes, measured according to sections C and D above, may be used to adjust the varying intensities of the EEs. This procedure can be helpful as the working amplitudes may decrease due to material fatigue over time of wearing albeit the patient exercised with equal intensity.

The allocation of the patient activity to a value of the AI scale (e.g. 4 on a 1-10 scale) can be predefined by the monitoring system 116. Further, the therapist may adjust this AI allocation according to the physical condition of the patient. For example, a patient with a significant walking disability may have the same definition for EEs to maintain comparability. However, the AI scale can be less stringent to maintain enough resolution even for low activity profiles.

In parallel to the Activity Index generated by pressure gradients, also a motion sensor placed on the leg, foot or other parts of the body may be added to the monitoring system 116. This motion sensor may be capable of tracking continuous information about movements. This information can be used to complete the AI profile. Also, the motion sensor can be used to activate the "sleep" modus in case no activity is detected. In this case, the interval from one single measurement to the next measurement will be increased to prolong the life of a battery.

Patient Coaching

The description above summarizes how the activity profile may be recorded to allow the therapist appropriate medical judgement and consecutive instructions for the patient. In a further step, the monitoring system 116 could also coach the patient to achieve good physical activity for optimal compression effects.

For this purpose, the therapist might feed the system with a minimum required AI rate for a predefined time interval. With e.g. an acoustical signal, the monitoring system 116 may confirm acceptable activity, or in opposite demand further movement to optimize the action of the compression system. With a green, yellow, or red light or a smiley, the patient may be informed about the current activity achievement.

Further, as outlined above, a motion sensor could add information about the activity profile of the patient.

H.) Continuous Safety Surveillance System of Critical Overpressure

Typically, a high pressure exerted by the compression device 112 is rather uncritical, as long as the overpressure lasts for a short period only. This is typically observed if patients walk or do other physical activity. However, if the pressure is continuously high, e.g. in the supine position at night, there is a risk for pressure related skin damage. For safety reasons it is therefore useful to optionally provide a warning in case the pressure exceeds a defined threshold value, such as for a longer time period.

As an example of a safety surveillance system which may be implemented into the monitoring system 116, the pressure may be recorded automatically. High pressure may be defined as a pressure exceeding a predetermined threshold, such as a pressure exceeding a threshold of 60 mmHg, preferably 80 mmHg, most preferably 100 mmHg. A warning may be created by the monitoring system 116 in case the pressure exceeds the predetermined threshold, such as for at least a predetermined time period. Thus, as an example, in case the pressure is continuously higher than e.g. 80 mmHg over a period of more than 1 s, preferably 120 s, most preferably 600 s, the monitoring system 116 may provide a warning, such as by an output of an acoustic signal and/or a visual signal. In such a case, the patient should change the position or walk, or move toes or the limb. In many cases, this can already change the applied forces exerted by the compression device 112. In a worst case, if changing the body position of movement does not help, the patient may have to remove the compression device 112, such as the compression bandage, or may have to reduce the tension in case of an adjustable compression system 110.

In case of a coincident disease, e.g. peripheral arterial occlusive disease, pressure may be more critical. In this case, the therapist may adjust the threshold for pressure and the time of pressure according to the patient's needs.

I.) Continuous Surveillance of Insufficient Pressure Profiles

As outlined above, resting and standing pressure (including extended standing pressure) as well as pressure amplitudes may be measured, such as by a nurse, a physician, a therapist or any other medical staff. For this procedure, the patient may be instructed to change to the needed body position.

In order to allow for an assessment of compression efficacy independently from any therapist or clinical visit, the monitoring system 116 may also continuously monitor the pressure profiles and, hence, the efficacy of the compression device 112. Therein, various options exist. Several potential options are described below:

Option 1: Once a day (such as 1-20 times a day) the patient may initiate a measurement, such as by pressing a button on the monitoring system 116, and will assume a resting position, such as by assuming a supine position, as described in section A above. The monitoring system 116 may automatically measure the resting pressure, such as once the measurement curve has stabilized. Subsequently, the evaluation unit 126 may invite the patient to change a position. Thus, an acoustic signal may be provided to the patient. The patient may then change into the standing position, and the monitoring system 116 will again measure the pressure, preferably automatically. The results of $p_{rest2}$ and $p_{standing2}$ and/or $p_{rest2}$ and $p_{standing, extended2}$ may be compared to the initial data $p_{rest1}$ and $p_{standing1}$ and/or $p_{rest1}$ and $p_{standing, extended1}$, preferably automatically. A difference between the baseline ($p_{rest1}$ and $p_{standing1}$ and/or $p_{rest1}$ and $p_{standing, extended1}$) and follow-up measurements ($p_{rest2}$ and $p_{standing2}$ and/or $p_{rest2}$ and $p_{standing, extended2}$) may be processed, such as disclosed above in sections A and B.

The same procedure may be performed with one or more of the SSI, the ESSI and the pressure amplitude, as disclosed in sections C above and D.

As previously discussed, the monitoring system 116 may indicate if the compression device 112, such as the compression bandage, is not effective any more.

Option 2: Once a day (such as 1-20 times a day) the monitoring system 116 may provide an invitation to the patient, such as by providing an acoustic signal. After that, the patient may change to a resting position, such as to the supine position, and, later on, to the standing and/or walking position as described above under 1.

Option 3: For permanent assessment of the efficacy of the compression device 112, the monitoring system 116 may continuously measure the pressure. The monitoring system 116 may acquire measurement curves and may detect the standing pressure and/or the extended standing pressure, such as by evaluating the asymptotic behavior of the measurement curve, as disclosed above in sections A and B. An asymptotic function typically is only detected if the patient is at rest, e.g. in supine or sitting position, and/or if the patient is standing without significant movement. In the supine position, the lowest pressure curves are expected.

By detecting the lowest pressure value in the measurement curve, and, further, by assuming that this lowest pressure value is measured in a resting position, specifically in a supine position, the lowest pressure value may be recorded. Thus, as an example, the lowest pressure value acquired within 1 h up to 1 day, preferably 12 h, may be recorded as the actual resting pressure $p_{min}$. In parallel, the same procedure optionally may be performed with the maximum asymptotic pressure curve. This value may be recorded as $p_{max}$. The difference of $p_{min}$ and $p_{max}$ may be defined as $\Delta p$:

$$p_{max} - p_{min} = \Delta p$$

$\Delta p$ typically only provides a very rough approximation of the SSI or ESSI, respectively. It may be desirable to compare a $\Delta p$ of the first day ($\Delta p_1$) with a $\Delta p$ of the second day ($\Delta p_2$). The monitoring system 116 may indicate inefficacy, if the difference between $\Delta p_1$ and $\Delta p_2$ is greater than a predetermined threshold, such as 3 mmHg, preferably 10 mmHg:

$$\Delta p_1 - \Delta p_2 > 3 \text{ mmHg (preferably} > 10 \text{ mmHg)} \rightarrow \text{change compression}$$

Further, additionally or alternatively, relative changes may be used to define inefficacy. Thus, pressure changes $\Delta p_1$ and $\Delta p_2$ measured at different points in time may be compared. Thus, again, a ratio of these pressure changes may be formed and may be compared to one or more threshold values. As an example, the monitoring system 116 may indicate an inefficacy of the compression device 112 in case $\Delta p_2$ is less than 80% (preferably less than 60%), as compared to $\Delta p_1$:

$$(\Delta p_2 / \Delta p_1) \times 100\% < 80\%, \text{ preferably} < 60\% \rightarrow \text{change compression}$$

Option 4: A further optional method for assessment if the compression device 112 is still effective may be the assessment of amplitudes when the patient performs a particular activity, such as walking, as described in detail above in Section D.

Position of the Pressure Sensor 118

A single pressure sensor 118 may be applied at the medial aspect of the lower leg, at the transition of the gastrocnemius muscle into the Achilles tendon. This position is denoted by B1 in FIG. 8 and is situated typically approximately 10-15 cm proximal to the medial malleolus.

As this point covers only a small anatomical area, it is easy to imagine that a pressure sensor 118 may easily be misplaced.

Positioning a pressure sensor 118 on the muscular part of the calf (position C in FIG. 8) is less sensitive. Therefore, another option is to position the pressure sensor 118 on the calf muscles. Threshold values as provided in sections A-D above might be changed in accordance to the actual placement of the pressure sensor 118 and/or in accordance with the anatomical area in which the pressure sensor 118 is placed. The above-mentioned thresholds, however, are preferred for the B1 position.

Also a plurality of pressure sensors 118 may be used in order to assess pressure at several areas. Further, one or more large area pressure sensors 118 might be used. Thus, as an example, one big wide pressure sensor 118 may be used which covers the whole leg. This pressure sensor 118 might be capable of measuring the pressure under relevant portions or even under the whole surface of the compression device 112. The at least one pressure sensor 118 and/or the pressure sensor positions defined above may be used for all described methods to measure compression efficacy.

The invention claimed is:

1. A monitoring system for determining the efficacy of a compression therapy device, comprising:
   at least one pressure sensor; and
   at least one evaluation unit that is configured to connect with the at least one pressure sensor and that is configured to:
      receive first data, from the at least one pressure sensor, that represents force exerted by the compression therapy device onto a body part of a user while the user is in a supine position;
      calculate, from the first data, a first pressure value for determining the efficacy of the compression therapy device;
      receive second data, from the at least one pressure sensor, that represents force exerted by the compression therapy device onto the body part of the user while the user is in a non-supine position;
      calculate, from the second data, a second pressure value for determining the efficacy of the compression therapy device by at least:
         detecting when the rate of change in the second data is less than or equal to a programmable threshold value; and
         assigning the second pressure value to a variable defined as an extended standing pressure for determining the efficacy of the compression therapy device,
      wherein the second pressure value is a function of a time at which the rate of change in the second data is less than or equal to the programmable threshold value; and
      output at least one of an audio cue signal and a visual cue signal that represents efficacy of the compression therapy device responsive to a determination that a relational criterion between the second pressure value and the first pressure value is met.

2. The monitoring system according to claim 1, wherein the evaluation unit is configured to acquire pressure values from the at least one pressure sensor responsive to a position change of the user.

3. The monitoring system according to claim 1, wherein the evaluation unit is configured to determine at least one key figure K from pressure values provided by the at least one pressure sensor, wherein the at least one key figure K is a factor for determining the efficacy of the compression therapy device.

4. The monitoring system according to claim 3, wherein the evaluation unit is configured to compare the at least one key figure K to at least one efficacy threshold for automatically determining the efficacy of the compression therapy device.

5. The monitoring system according to claim 3, wherein the evaluation unit is configured to determine at least two different key figures $K_1$ and $K_2$ from pressure values provided by the at least one pressure sensor, and wherein the evaluation unit is configured to automatically determine the efficacy of the compression therapy device from the at least two different key figures $K_1$ and $K_2$.

6. The monitoring system according to claim 3, wherein the extended standing pressure is the extended standing pressure $p_{standing, extended}$ and the key figure is selected from the group consisting of:
   a resting pressure $p_{rest}$;
   a standing pressure $p_{standing}$ with the user being in a standing position;
   a baseline resting pressure $p_{rest, baseline}$ directly after application of the compression system;
   the extended standing pressure $p_{standing, extended}$;
   a static stiffness index SSI, the static stiffness index being determined by subtracting the resting pressure $p_{rest}$ from a standing pressure $p_{standing}$;
   an extended static stiffness index ESSI, the extended static stiffness index being determined by subtracting the resting pressure $p_{rest}$ from the extended standing pressure $p_{standing, extended}$;
   a difference $ESSI_1 - ESSI_2$ between at least two extended static stiffness indices $ESSI_1$ and $ESSI_2$, the extended static stiffness index $ESSI_1$ being determined by subtracting a first resting pressure $p_{rest1}$ from a first extended standing pressure $p_{standing, extended\ 1}$, the extended static stiffness index $ESSI_2$ being determined by subtracting a second resting pressure $p_{rest2}$ from a second extended standing pressure $p_{standing, extended\ 2}$;
   a difference $SSI_1 - SSI_2$ between at least two static stiffness indices $SSI_1$ and $SSI_2$, the static stiffness index $SSI_1$ being determined by subtracting a first resting pressure $p_{rest1}$ from a first standing pressure $p_{standing1}$, the static stiffness index $SSI_2$ being determined by subtracting a second resting pressure $p_{rest2}$ from a second standing pressure $p_{standing2}$;
   a ratio $ESSI_1 : ESSI_2$ of at least two extended static stiffness indices $ESSI_1$ and $ESSI_2$, the extended static stiffness index $ESSI_1$ being determined by subtracting a first resting pressure $p_{rest1}$ from a first extended standing pressure $p_{standing, extended\ 1}$, the extended static stiffness index $ESSI_2$ being determined by subtracting a second resting pressure $p_{rest2}$ from a second extended standing pressure $p_{standing, extended\ 2}$;
   a ratio $SSI_1 : SSI_2$ of at least two static stiffness indices $SSI_1$ and $SSI_2$, the static stiffness index $SSI_1$ being determined by subtracting a first resting pressure $p_{rest1}$ from a first standing pressure $p_{standing1}$, the static stiffness index $SSI_2$ being determined by subtracting a second resting pressure $p_{rest2}$ from a second standing pressure $p_{standing2}$;

a difference between at least two resting pressures $p_{rest1}$ and $p_{rest2}$ acquired at at least two different points in time;

a ratio between at least two resting pressures $p_{rest1}$ and $p_{rest2}$ acquired at at least two different points in time;

a difference between at least two extended standing pressures $p_{standing, extended\ 1}$ and $p_{standing, extended\ 2}$ acquired at at least two different points in time;

a difference between at least two standing pressures and $p_{standing1}$ and $p_{standing2}$ acquired at at least two different points in time;

a ratio of at least two extended standing pressures $p_{standing, extended\ 1}$ and $p_{standing, extended\ 2}$ acquired at at least two different points in time;

a ratio of at least two standing pressures $p_{standing1}$ and $p_{standing2}$ acquired at at least two different points in time;

a median or mean amplitude of a measurement curve of pressure values acquired during a defined movement of the user;

a ratio of at least one first median or mean amplitude ($Amplitude_{median1}$ or $Amplitude_{mean1}$) of a first measurement curve of pressure values acquired during a first defined movement of the user and at least one second median or mean amplitude ($Amplitude_{median2}$ or $Amplitude_{mean2}$) of a second measurement curve of pressure values acquired during a second defined movement of the user;

a refilling time $t_{refill}$ for vein refilling after a change of position from a resting position into a standing position;

a difference $t_{refill1} - t_{refill2}$ between at least one first refilling time $t_{refill1}$ for vein refilling after a first change of position from a resting position into a standing position and at least one second refilling time $t_{refill2}$ for vein refilling after a first change of position from a resting position into a standing position;

a ratio $t_{refill1}:t_{refill2}$ of at least one first refilling time $t_{refill1}$ for vein refilling after a first change of position from a resting position into a standing position and at least one second refilling time $t_{refill2}$ for vein refilling after a first change of position from a resting position into a standing position;

a parameter derived from a refilling curve, the refilling curve being a measurement curve acquired after a change of position from a resting position into a standing position, specifically a parameter indicating at least one of a slope of the refilling curve and a shape of the refilling curve.

7. The monitoring system according to claim 3, wherein the at least one of the audio cue signal and the visual cue signal represents a warning that the at least one key figure K is outside an admissible range.

8. The monitoring system according to claim 1, wherein the monitoring system is configured to prompt the user through at least one measurement routine.

9. The monitoring system according to claim 1, wherein the evaluation unit is configured to recognize at least one predetermined type of movement of the user by evaluating a measurement curve of pressure values.

10. The monitoring system according to claim 1, wherein the evaluation unit is configured to store an activity profile of the user.

11. The monitoring system according to claim 1, wherein the at least one pressure sensor is selected from the group consisting of: a semiconductor pressure sensor; a pressure sensor having a deformation-sensitive resistor; a pressure sensor having a deformation-sensitive capacitor; a pressure sensor having a deformation-sensitive light guide; and a pressure sensor having a fluid-filled bladder.

12. The monitoring system according to claim 1, wherein the evaluation unit is configured to detect arterial pulsations in a measurement curve of pressure values provided by the at least one pressure sensor.

13. A method for determining the efficacy of a compression therapy device by an evaluation unit that is configured to connect with at least one pressure sensor, comprising:
receiving first data, from the at least one pressure sensor, that represents force exerted by the compression therapy device onto a body part of a user while the user is in a supine position;
calculating, from the first data, a first pressure value for determining the efficacy of the compression therapy device;
receiving second data, from the at least one pressure sensor, that represents force exerted by the compression therapy device onto the body part of the user while the user is in a non-supine position;
calculating, from the second data, a second pressure value for determining the efficacy of the compression therapy device by at least:
detecting when the rate of change in the second data is less than or equal to a programmable threshold value; and
assigning the second pressure value to a variable defined as an extended standing pressure for determining the efficacy of the compression therapy device,
wherein the second pressure value is a function of a time at which rate of change in the second data is less than or equal to a programmable threshold value; and
outputting at least one of an audio cue signal and a visual cue signal that represents efficacy of the compression therapy device responsive to a determination that a relational criterion between the second pressure value and the first pressure value is met.

14. The method according to claim 13, further comprising determining at least one key figure K from pressure values provided by the pressure sensor, wherein the at least one key figure is a factor for determining the efficacy of the compression therapy device.

15. The method according to claim 13, further comprising generating the at least one of the audio cue signal and the visual cue signal to exhibit a characteristic that represents an instruction to exchange the compression therapy device.

* * * * *

UNITED STATES PATENT AND TRADEMARK OFFICE
CERTIFICATE OF CORRECTION

PATENT NO. : 9,968,294 B2
APPLICATION NO. : 14/437549
DATED : May 15, 2018
INVENTOR(S) : Jens Bichel et al.

It is certified that error appears in the above-identified patent and that said Letters Patent is hereby corrected as shown below:

In the Specification

Column 24
Line 57 (Approx.)          Delete "22" and insert -- > --, therefor.

Column 26
Line 59                    Delete "as as" and insert -- as --, therefor.

Column 33
Line 23                    After "values" insert -- . --.

In the Claims

Column 40
Line 26                    In Claim 6, delete "$p_{standing\,,\,extended}$" and insert -- $p_{standing,\,extended}$ --, therefor.
Line 45                    In Claim 6, delete "$p_{standing\,,\,extended}$" and insert -- $p_{standing,\,extended}$ --, therefor.
Line 48                    In Claim 6, delete "$p_{standing\,,\,extended\,2}$" and insert -- $p_{standing,\,extended\,2}$ --, therefor.
Line 51                    In Claim 6, delete "$SSI_1 being$" and insert -- $SSI_1$ being --, therefor.
Line 60                    In Claim 6, delete "$p_{standing\,,\,extended\,1}$" and insert -- $p_{standing,\,extended\,1}$ --, therefor.
Line 63                    In Claim 6, delete "$p_{standing\,,\,extended\,2}$" and insert -- $p_{standing,\,extended\,2}$ --, therefor.

Column 41
Line 10 (Approx.)          In Claim 6, delete "$p_{standing\,,\,extended\,1}$" and insert -- $p_{standing,\,extended\,1}$ --, therefor.

Signed and Sealed this
Ninth Day of October, 2018

Andrei Iancu
*Director of the United States Patent and Trademark Office*

CERTIFICATE OF CORRECTION (continued)
U.S. Pat. No. 9,968,294 B2

| | |
|---|---|
| Line 12 (Approx.) | In Claim 6, after "pressures" delete "and". |
| Line 16 (Approx.) | In Claim 6, delete "$p_{pstanding,\ extended\ 1}$" and insert -- $p_{standing,\ extended\ 1}$ --, therefor. |
| Line 16 (Approx.) | In Claim 6, delete "$p_{standing,\ extended\ 2}acquired$" and insert -- $p_{standing,\ extended\ 2}$ acquired --, therefor. |